(12) United States Patent
Gillis et al.

(10) Patent No.: US 8,327,854 B2
(45) Date of Patent: Dec. 11, 2012

(54) PARTIALLY ERODABLE SYSTEMS FOR TREATMENT OF OBSTRUCTIVE SLEEP APNEA

(75) Inventors: Edward M. Gillis, San Jose, CA (US); Octavian Iancea, Sunnyvale, CA (US)

(73) Assignee: ReVent Medical, Inc., Cupertino, CA (US)

( * ) Notice: Subject to any disclaimer, the term of this patent is extended or adjusted under 35 U.S.C. 154(b) by 0 days.

(21) Appl. No.: 13/269,520

(22) Filed: Oct. 7, 2011

(65) Prior Publication Data

US 2012/0024298 A1 Feb. 2, 2012

Related U.S. Application Data

(63) Continuation of application No. 12/937,564, filed as application No. PCT/US2009/043450 on May 11, 2009.

(60) Provisional application No. 61/052,586, filed on May 12, 2008.

(51) Int. Cl.
*A61F 5/56* (2006.01)
(52) U.S. Cl. .................. 128/848; 128/897; 128/898
(58) Field of Classification Search .................. 128/848, 128/897, 898; 623/9, 11.11, 14.11
See application file for complete search history.

(56) References Cited

U.S. PATENT DOCUMENTS

| | | | |
|---|---|---|---|
| 4,424,208 A | 1/1984 | Wallace et al. | |
| 4,582,640 A | 4/1986 | Smestad et al. | |
| 4,978,323 A | 12/1990 | Freedman | |
| 5,041,138 A | 8/1991 | Vacanti et al. | |
| 5,145,935 A | 9/1992 | Hayashi | |
| 5,326,355 A | 7/1994 | Landi | |
| 5,428,024 A | 6/1995 | Chu et al. | |
| 5,506,300 A | 4/1996 | Ward et al. | |
| 5,665,822 A | 9/1997 | Bitler et al. | |
| 5,697,779 A | 12/1997 | Sachdeva et al. | |
| 5,762,599 A | 6/1998 | Sohn | |
| 5,972,000 A | 10/1999 | Beyar et al. | |
| 5,979,456 A | 11/1999 | Magovern | |
| 5,988,171 A | 11/1999 | Sohn et al. | |
| 6,019,779 A | 2/2000 | Thorud et al. | |
| 6,161,541 A | 12/2000 | Woodson | |
| 6,165,486 A | 12/2000 | Marra et al. | |
| 6,231,605 B1 | 5/2001 | Ku | |

(Continued)

FOREIGN PATENT DOCUMENTS

EP  1216013 B1  6/2006

(Continued)

OTHER PUBLICATIONS

Jeon et al.; Shape memory and nonostructure in poly(norbornyl-POSS) copolymers; Polym Int; vol. 49; pp. 453-457; 2000.

(Continued)

*Primary Examiner* — Patricia Bianco
*Assistant Examiner* — Camtu Nguyen
(74) *Attorney, Agent, or Firm* — Shay Glenn LLP

(57) ABSTRACT

A method of maintaining airway patency in an airway of a patient which includes the steps of implanting a device into tissue adjacent an airway, the device having a bioerodable material wound around a resiliently deformable body to temporarily maintain the deformable body in a stretched, deformed state, and permitting the bioerodable material of the device to bioerode to apply a force to maintain airway patency. The invention also provides devices for practicing the method.

28 Claims, 24 Drawing Sheets

U.S. PATENT DOCUMENTS

| | | | |
|---|---|---|---|
| 6,250,307 B1 | 6/2001 | Conrad et al. | |
| 6,388,043 B1 | 5/2002 | Langer et al. | |
| 6,390,096 B1 * | 5/2002 | Conrad et al. | 128/897 |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,439,238 B1 | 8/2002 | Brenzel et al. | |
| 6,450,169 B1 | 9/2002 | Conrad et al. | |
| 6,453,905 B1 | 9/2002 | Conrad et al. | |
| 6,458,127 B1 | 10/2002 | Truckai et al. | |
| 6,467,485 B1 | 10/2002 | Schmidt | |
| 6,502,574 B2 | 1/2003 | Stevens et al. | |
| 6,507,675 B1 | 1/2003 | Lee et al. | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,541 B2 | 2/2003 | Knudson et al. | |
| 6,523,542 B2 | 2/2003 | Knudson et al. | |
| 6,546,936 B2 | 4/2003 | Knudson et al. | |
| 6,569,191 B1 | 5/2003 | Hogan | |
| 6,578,580 B2 | 6/2003 | Conrad et al. | |
| 6,578,763 B1 | 6/2003 | Brown | |
| 6,601,584 B2 | 8/2003 | Knudson et al. | |
| 6,626,181 B2 | 9/2003 | Knudson et al. | |
| 6,629,988 B2 | 10/2003 | Weadock | |
| 6,634,362 B2 | 10/2003 | Conrad et al. | |
| 6,636,767 B1 | 10/2003 | Knudson et al. | |
| 6,703,040 B2 | 3/2004 | Katsarava et al. | |
| 6,748,950 B2 | 6/2004 | Clark et al. | |
| 6,748,951 B1 | 6/2004 | Schmidt | |
| 6,772,944 B2 | 8/2004 | Brown | |
| 6,899,105 B2 * | 5/2005 | Krueger et al. | 128/897 |
| 7,017,582 B2 | 3/2006 | Metzger et al. | |
| 7,063,089 B2 | 6/2006 | Knudson et al. | |
| 7,090,672 B2 | 8/2006 | Underwood et al. | |
| 7,107,992 B2 | 9/2006 | Brooks et al. | |
| D536,792 S | 2/2007 | Krueger et al. | |
| 7,192,443 B2 | 3/2007 | Solem et al. | |
| 7,213,599 B2 | 5/2007 | Conrad et al. | |
| 7,255,110 B2 | 8/2007 | Knudson et al. | |
| 7,322,356 B2 | 1/2008 | Critzer et al. | |
| 7,337,781 B2 | 3/2008 | Vassallo | |
| 7,824,704 B2 | 11/2010 | Anderson et al. | |
| 7,909,037 B2 | 3/2011 | Hegde et al. | |
| 7,909,038 B2 | 3/2011 | Hegde et al. | |
| 7,947,076 B2 | 5/2011 | Vassallo et al. | |
| 7,992,567 B2 | 8/2011 | Hirotsuka et al. | |
| 7,997,266 B2 | 8/2011 | Frazier et al. | |
| 2002/0116050 A1 | 8/2002 | Kocur | |
| 2003/0149445 A1 | 8/2003 | Knudson et al. | |
| 2004/0045556 A1 | 3/2004 | Nelson et al. | |
| 2004/0139975 A1 | 7/2004 | Nelson et al. | |
| 2005/0004417 A1 | 1/2005 | Nelson et al. | |
| 2005/0065615 A1 | 3/2005 | Krueger et al. | |
| 2005/0092332 A1 | 5/2005 | Conrad et al. | |
| 2005/0115572 A1 | 6/2005 | Brooks et al. | |
| 2005/0121039 A1 | 6/2005 | Brooks et al. | |
| 2005/0154412 A1 | 7/2005 | Krueger et al. | |
| 2005/0267321 A1 | 12/2005 | Shadduck | |
| 2006/0150986 A1 | 7/2006 | Roue et al. | |
| 2006/0201519 A1 | 9/2006 | Frazier et al. | |
| 2006/0207606 A1 | 9/2006 | Roue et al. | |
| 2006/0229669 A1 | 10/2006 | Mirizzi et al. | |
| 2006/0235380 A1 | 10/2006 | Vassallo | |
| 2006/0260623 A1 | 11/2006 | Brooks et al. | |
| 2006/0289014 A1 | 12/2006 | Purdy et al. | |
| 2006/0289015 A1 | 12/2006 | Boucher et al. | |
| 2007/0144534 A1 | 6/2007 | Mery et al. | |
| 2007/0261701 A1 | 11/2007 | Sanders | |
| 2007/0288057 A1 | 12/2007 | Kuhnel | |
| 2007/0295340 A1 | 12/2007 | Buscemi | |
| 2008/0023012 A1 | 1/2008 | Dineen et al. | |
| 2008/0027560 A1 | 1/2008 | Jackson et al. | |
| 2008/0053461 A1 | 3/2008 | Hirotsuka et al. | |
| 2008/0058584 A1 | 3/2008 | Hirotsuka et al. | |
| 2008/0066764 A1 | 3/2008 | Paraschac et al. | |
| 2008/0066765 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 | 4/2008 | Buscemi et al. | |
| 2008/0078412 A1 | 4/2008 | Buscemi et al. | |
| 2008/0082113 A1 | 4/2008 | Bishop et al. | |
| 2008/0188947 A1 | 8/2008 | Sanders | |
| 2009/0038623 A1 | 2/2009 | Farbarik et al. | |
| 2009/0044814 A1 | 2/2009 | Iancea et al. | |
| 2009/0126742 A1 | 5/2009 | Summer | |
| 2009/0177027 A1 | 7/2009 | Gillis | |
| 2009/0319046 A1 | 12/2009 | Krespi et al. | |
| 2010/0037901 A1 | 2/2010 | Rousseau et al. | |
| 2010/0132719 A1 | 6/2010 | Jacobs et al. | |
| 2010/0158854 A1 | 6/2010 | Puisais | |
| 2011/0144421 A1 | 6/2011 | Gillis | |
| 2011/0174315 A1 | 7/2011 | Zhang et al. | |

FOREIGN PATENT DOCUMENTS

| | | |
|---|---|---|
| WO | WO 97/18854 A1 | 5/1997 |
| WO | WO 99/00058 A1 | 1/1999 |
| WO | WO 00/66050 A1 | 11/2000 |
| WO | WO 01/89426 A1 | 11/2001 |
| WO | WO 02/76341 A2 | 2/2002 |
| WO | WO 02/013738 A1 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/055417 A1 | 7/2003 |
| WO | WO 03/065947 A1 | 8/2003 |
| WO | WO 2005/044158 A1 | 5/2005 |
| WO | WO 2006/012188 A1 | 2/2006 |
| WO | WO 2006/093533 A1 | 9/2006 |
| WO | WO 2008/042058 A1 | 4/2008 |
| WO | WO 2008/097890 A2 | 8/2008 |
| WO | WO 2009/032625 A1 | 3/2009 |
| WO | WO 2010/028036 A1 | 3/2010 |
| WO | WO 2010/045546 A1 | 4/2010 |
| WO | WO 2010/051195 A1 | 5/2010 |

OTHER PUBLICATIONS

Lui et al.; Thermomechanical characterization of a tailored series of shape memory polymers; J Applied Med Polymers; vol. 6/ No. 2; pp. 47-52; 2002.

Mather et al.; Strain recovery in POSS hybrid thermoplastics; Polymer; vol. 41, No. 1; pp. 528-529; 2000.

Gillis et al.; U.S. Appl. No. 13/053,025 entitled "Systems and methods for treatment of sleep apnea," filed Mar. 21, 2011.

Gillis et al.; U.S. Appl No. 13/053,059 entitled "Systems and methods for treatment of sleep apnea," filed Mar. 21, 2011.

Gillis et al.; U.S. Appl. No. 13/113,933 entitled "Systems and methods for treatment of sleep apnea ," filed May 23, 2011.

Gillis et al.; U.S. Appl. No. 13/113,946 entitled "Systems and methods for treatment of sleep apnea ," filed May 23, 2011.

Gillis, Edward M.; U.S. Appl. No. 13/188,385 entitled "Systems and methods for treatment of sleep apnea ," filed Jul. 21, 2011.

Gillis, Edward M..; U.S. Appl. No. 13/308,449 entitled "Systems and methods for treatment of sleep apnea," filed Nov. 30, 2011.

Gillis et al.; U.S. Appl. No. 13/311,460 entitled "Systems and methods for treatment of sleep apnea," filed Dec. 5, 2011.

* cited by examiner

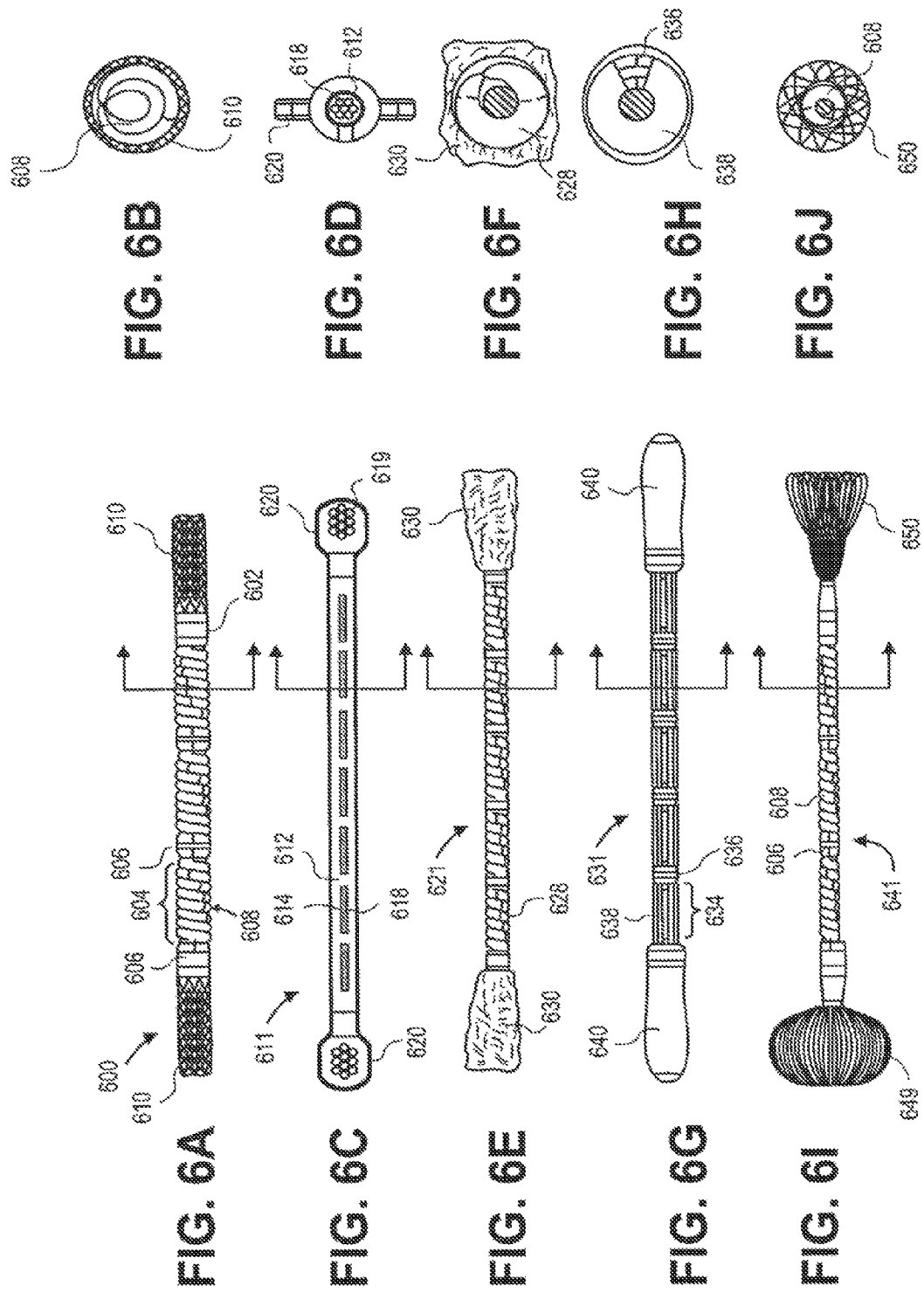

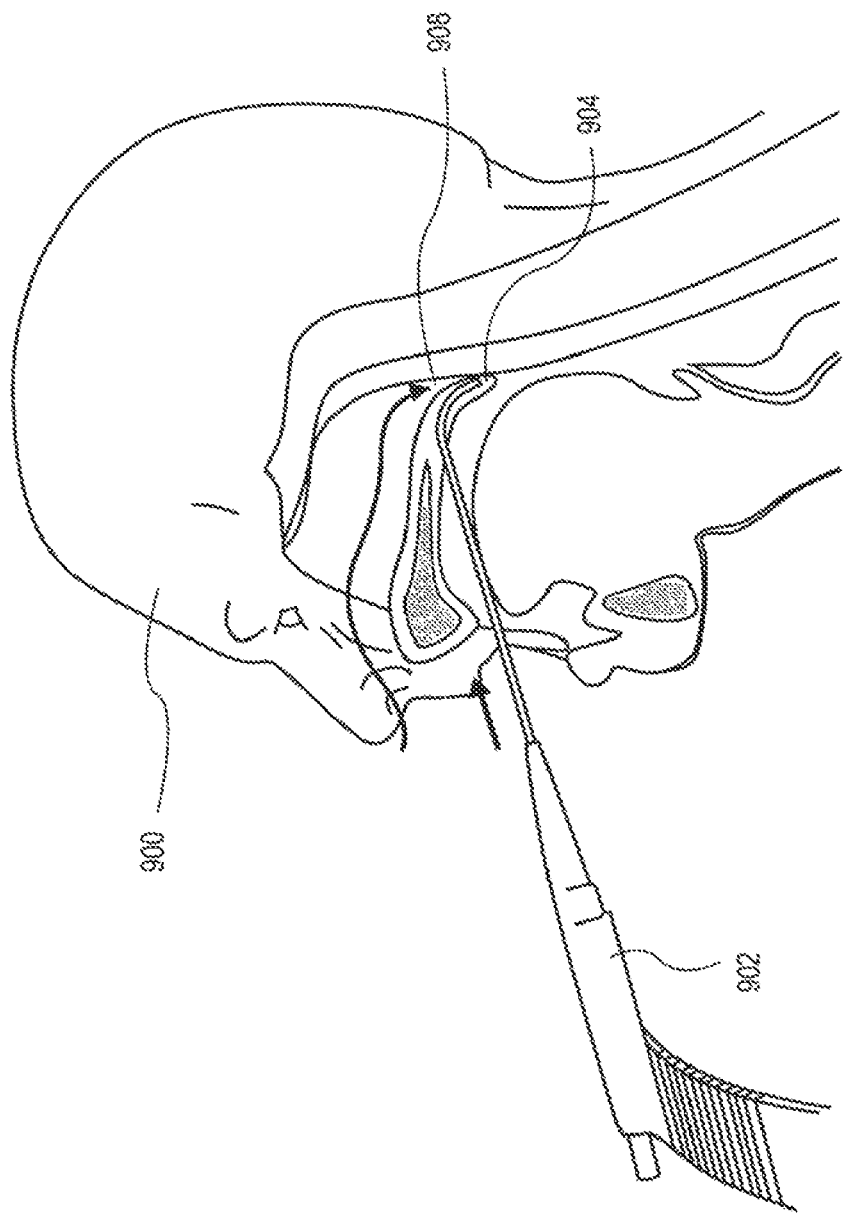

PARTIALLY ERODABLE SYSTEMS FOR TREATMENT OF OBSTRUCTIVE SLEEP APNEA

CROSS REFERENCE TO RELATED APPLICATIONS

This application is a continuation application which claims continuation and claims priority of U.S. application Ser. No. 12/937,564, filed on Jan. 3, 2011, which is a 371 patent application claiming priority of PCT Application No. PCT/US09/43450, filed on May 11, 2009, which claims the benefit under 35 U.S.C. §119(e) of U.S. Provisional Appl. No. 61/052,586, filed May 12, 2008, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The invention relates to the field of methods and devices for the treatment of obstructive sleep apnea, and more particularly to opening the airway of subjects with symptoms of obstructive sleep apnea.

Sleep apnea is defined as the cessation of breathing for ten seconds or longer during sleep. During normal sleep, the throat muscles relax and the airway narrows. During the sleep of a subject with obstructive sleep apnea (OSA), the upper airway narrows significantly more than normal, and during an apneic event, undergoes a complete collapse that stops airflow. In response to a lack of airflow, the subject is awakened at least to a degree sufficient to reinitiate breathing. Apneic events and the associated arousals can occur up to hundreds of times per night, and become highly disruptive of sleep. Obstructive sleep apnea is commonly but not exclusively associated with a heavy body type, a consequence of which is a narrowed oropharyngeal airway.

Cyclic oxygen desaturation and fragmented sleeping patterns lead to daytime sleepiness, the hallmark symptom of the disorder. Further consequences of sleep apnea may include chronic headaches and depression, as well as diminished facilities such as vigilance, concentration, memory, executive function, and physical dexterity. Ultimately, sleep apnea is highly correlated with increased mortality and life threatening comorbidities. Cardiology complications include hypertension, congestive heart failure, coronary artery disease, cardiac arrhythmias, and atrial fibrillation. OSA is a highly prevalent disease conditions in the United States. An estimated 18 million Americans suffer from OSA to degrees that range from mild to severe, many of whom are undiagnosed, at least in part because the afflicted subjects are often unaware of their own condition.

Treatment of OSA usually begins with suggested lifestyle changes, including weight loss and attention to sleeping habits (such as sleep position and pillow position), or the use of oral appliances that can be worn at night and help position the tongue away from the back of the airway. More aggressive physical interventions include the use of breathing assist systems (such as continuous positive airway pressure machines) that provide a positive pressure to the airway through a mask worn by the subject. In some cases, pharmaceutical interventions can be helpful, but they generally are directed toward countering daytime sleepiness and do not address the root cause. Some surgical interventions are available, such as nasal surgeries, tonsillectomy and/or adenoidectomy, reductions in the soft palate or the uvula or the tongue base, or advancing the tongue base by an attachment to the mandible and pulling the base forward. These surgical approaches can be quite invasive and thus have a last-resort aspect to them and simply do not reliably alleviate or cure the condition. There is a need for less invasive procedures that show promise for greater therapeutic reliability.

Related devices and methods are described in U.S. patent application Ser. No. 11/969,201, filed 3 Jan. 2008, the disclosure of which is incorporated herein by reference.

SUMMARY OF THE DISCLOSURE

The present invention provides methods and devices for treating obstructive sleep apnea. Embodiments of the invention include methods for opening a collapsed or obstructed airway with devices that can be implanted into various tissues that form the airway.

Embodiments of the devices include resiliently deformable materials and bioerodable materials. The deformable portion of the devices is first formed into a preferred shape which is then subsequently deformed and stabilized in that deformed shape by incorporation or application of bioerodable materials to create a device in its implantable form. Once implanted into a tissue site, and thus exposed to an aqueous environment and to cellular and enzymatic action, the bioerodable portions of the device erode, thereby allowing the deformable portion of the device to return toward an at-rest form. Embodiments of the method, in their simplest form, thus include implanting a device, the bioerodable portion of the device bioeroding, the device changing shape as a consequence of the bioeroding, and the tissue remodeling in accordance with the force being exerted by the shape changing of the device.

One aspect of the invention provides a method of maintaining airway patency in an airway of a patient. The method includes the steps of implanting a device into airway-forming tissue without affixing the device to the tissue and permitting a bioerodable portion of the device to bioerode to apply a force to the airway-forming tissue to maintain airway patency. In some embodiments, the method also includes the step of expanding a portion of the device without affixing the device to the tissue, such as by, for example, permitting the portion of the device to self-expand. In various embodiments, the implanting step may include the step of inserting the device into the patient submandibularly, sublingually, and/or intra-orally.

In some embodiments, the permitting step includes the step of changing a shape of the device when the bioerodable portion bioerodes, such as by changing a length, curvature and/or width of the device. The method may also include the step of permitting newly formed tissue to infiltrate the device, possibly with the newly formed tissue at least partially infiltrating the device prior to applying a force to the airway-forming tissue.

In various embodiments, the implanting step includes the step of inserting the device into tongue tissue, soft palate tissue, pharyngeal wall tissue and/or epiglottis tissue. The method may also include the step of releasing a bioactive agent from the bioerodable portion as it bioerodes.

Another aspect of the invention provides a device for maintaining patency of an airway of a patient. In some embodiments, the device has a body having an at-rest shape and a deformed shape, the body being adapted to be implanted into airway-forming tissue of the patient, and proximal and distal anchors adapted to be implanted into the airway-forming tissue, without affixing the device to the tissue, and to be infiltrated by tissue to affix the anchors to the airway-forming tissue, with at least one bioerodable element maintaining the body in the deformed shape against a return force and the body being configured to return toward the at-rest shape upon erosion of the bioerodable element. In various embodiments, the body is sized and shaped to be inserted into tongue tissue, into soft palate tissue, and/or into pharyngeal tissue.

In various embodiments, the bioerodable element includes a coil and/or a C-shaped element. In some embodiments, at least one of the proximal and distal anchors is adapted to expand, possibly through self-expansion. One or more of the anchors may contain woven and/or non-woven material and may include through-holes to permit tissue in-growth. One or more of the anchors may also contain braided material.

In some embodiments, the device's deformed shape is longer, straighter and/or wider than its at-rest shape. The device may also have an elutable bioactive agent in some embodiments.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-B show an airway-maintaining device according to another embodiment of the invention. FIG. 6B is an enlarged cross-section along the lines shown in FIG. 6A.

FIGS. 6C-D show an airway-maintaining device according to yet another embodiment of the invention. FIG. 6D is an enlarged cross-section along the lines shown in FIG. 6C.

FIGS. 6E-F show an airway-maintaining device according to still another embodiment of the invention. FIG. 6F is an enlarged cross-section along the lines shown in FIG. 6E.

FIGS. 6G-H show an airway-maintaining device according to another embodiment of the invention. FIG. 6H is an enlarged cross-section along the lines shown in FIG. 6G.

FIGS. 6I-J show an airway-maintaining device according to yet another embodiment of the invention. FIG. 6J is a cross-section along the lines shown in FIG. 6I.

FIGS. 9A-C show implantation and use of an airway-maintaining device delivered intraorally to the soft palate.

DETAILED DESCRIPTION

Figure 1:
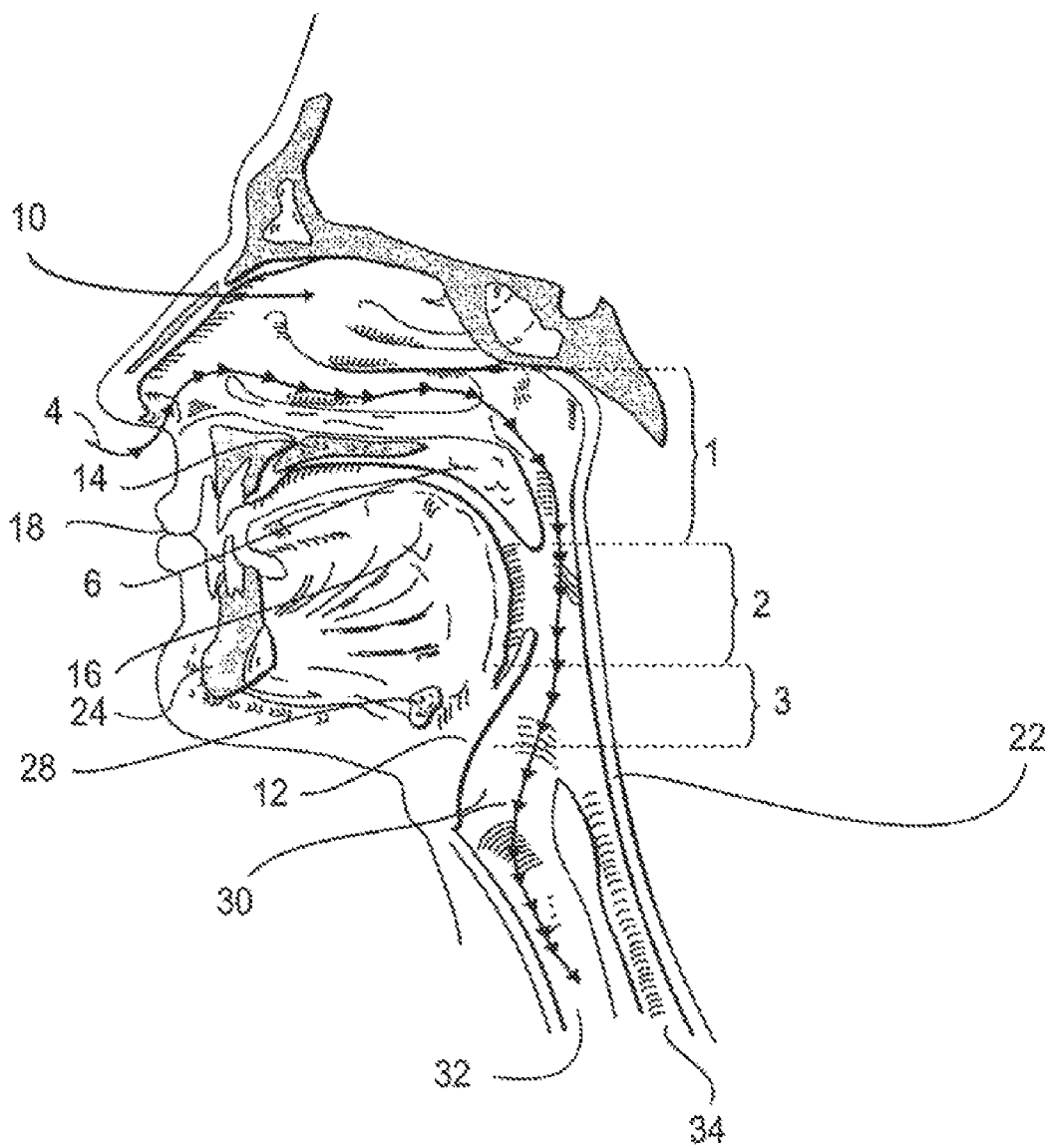
FIG. 1 shows an overview of the healthy human airway anatomy, with particular attention to the nasopharyngeal, oropharangeal, and hypopharyngeal regions.
Figure 2:
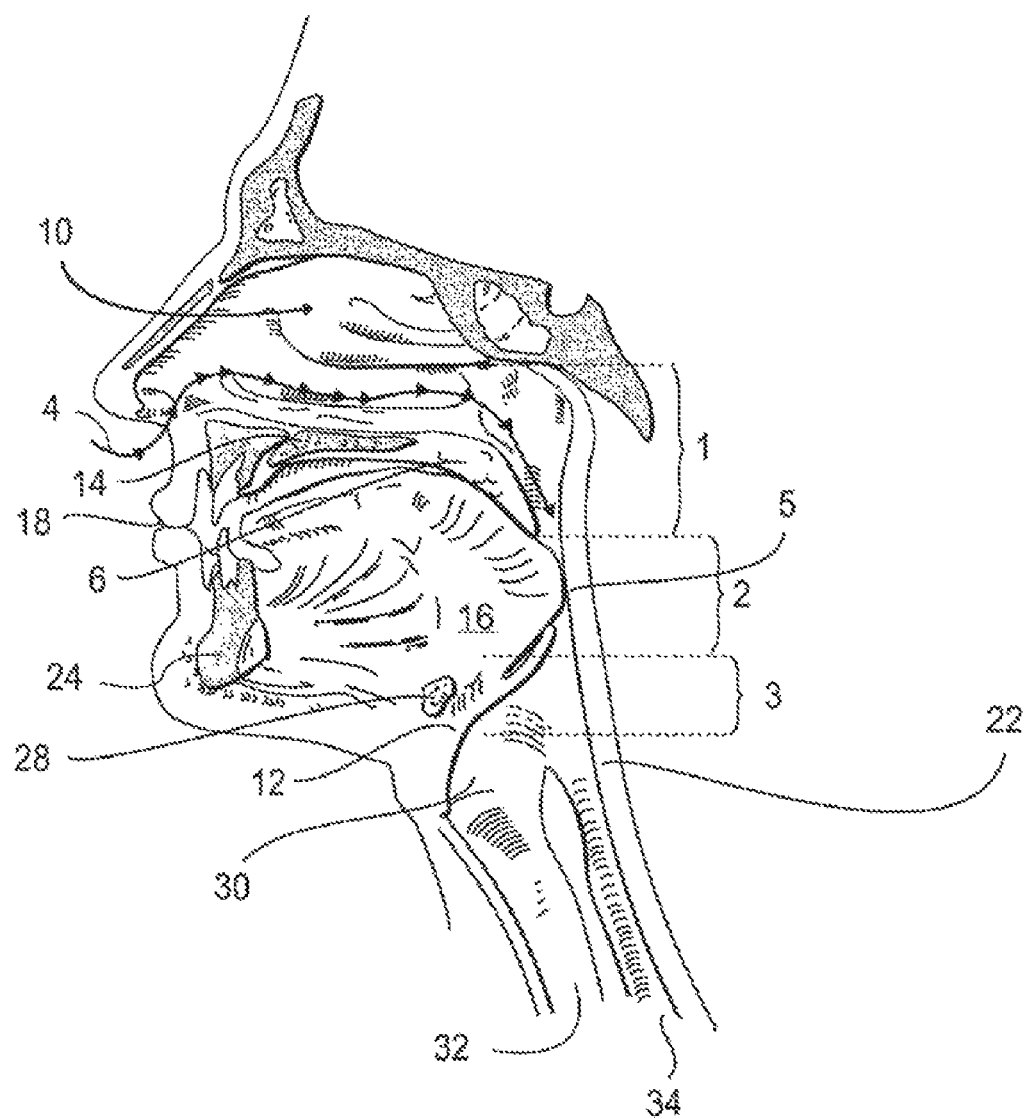
FIG. 2 provides a view of a compromised airway, with an occlusion in the oropharyngeal region due to posterior slippage of the base of the tongue and a thickened posterior pharyngeal wall.
Figure 3:
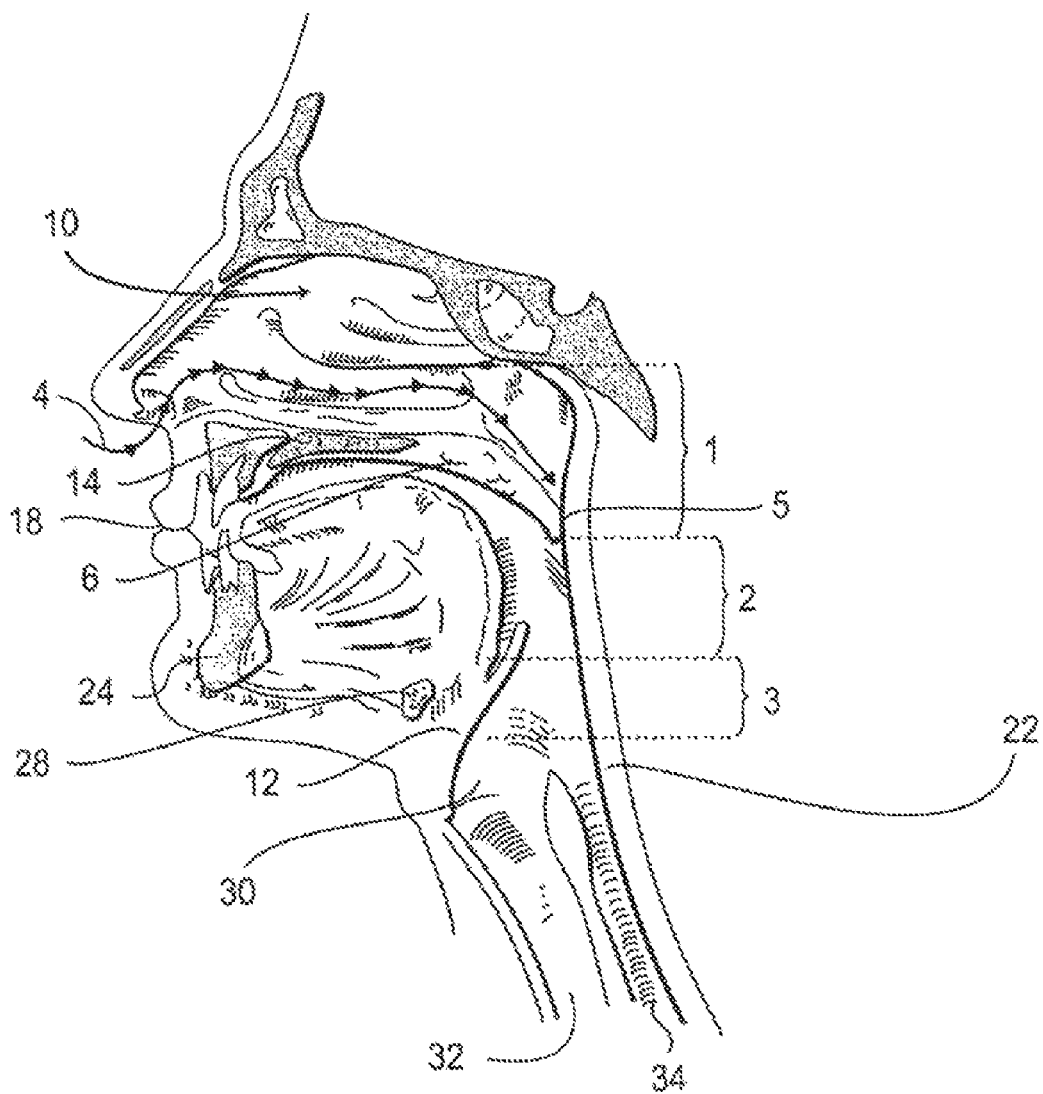
FIG. 3 provides a view of a compromised airway, with an occlusion in the nasopharyngeal region due to posterior slippage of the soft palate.
Figure 4:
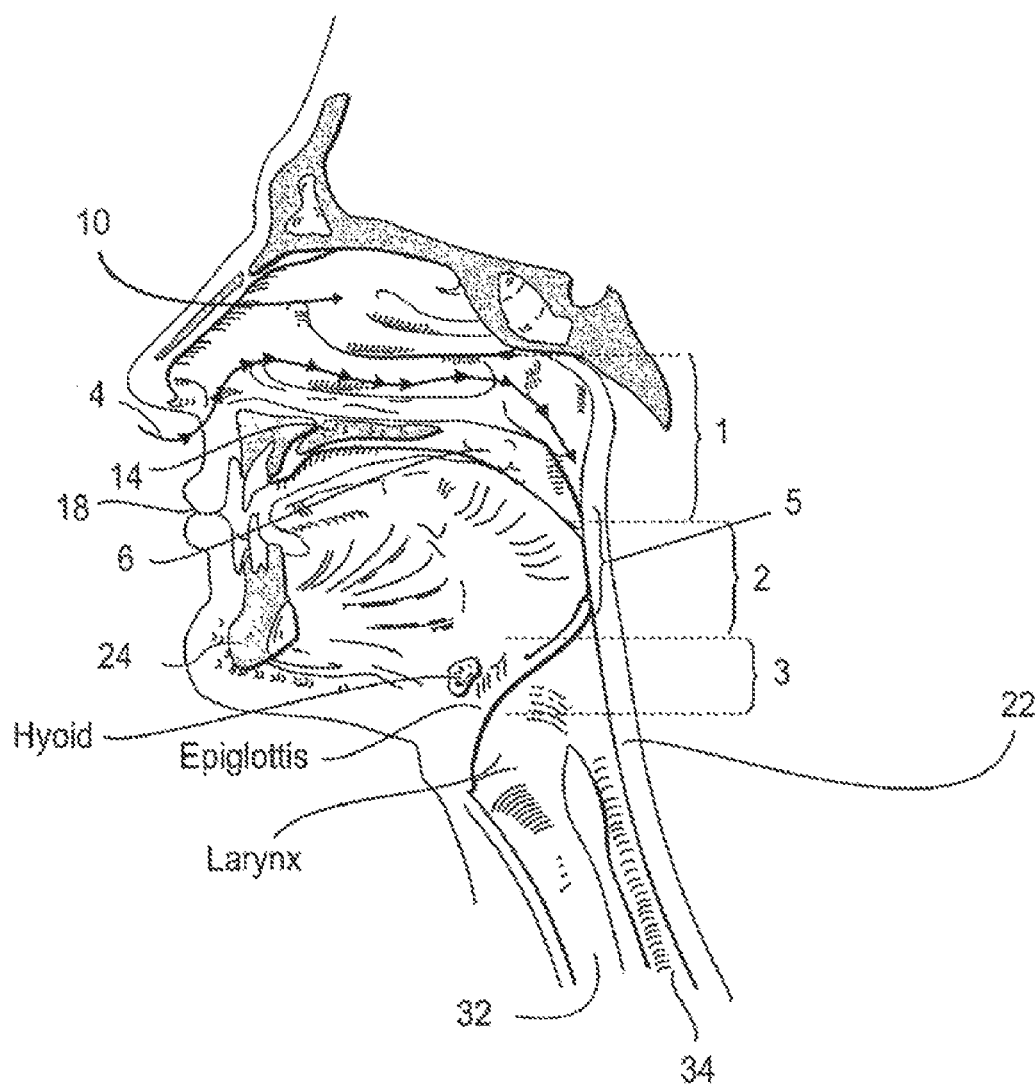
FIG. 4 provides a view of a compromised airway, with an occlusion in the oropharyngeal region due to posterior slippage of the base of the tongue and the soft palate, a thickened posterior pharyngeal wall, and posterior flopping of the epiglottis.

FIG. 1 is a sagittal view of the structures that form the pharyngeal airway 4. Some of these structures can become compromised under various conditions to the extent that they obstruct or occlude passage of air through the airway 4 and thus contribute to obstructive sleep apnea. The pharynx is divided, from superior to inferior, into the nasopharynx 1, the oropharynx 2 and the hypopharynx 3. Variations of FIG. 1 are provided in FIGS. 2, 3, and 4, which depict airway obstruction sites 5 at various levels in the pharyngeal airway. FIG. 2, for example, shows an occlusion 5 at the level of the oropharynx 2, where the base of the tongue 16 and a thickened posterior pharyngeal wall 22 have collapsed against each other. FIG. 3 shows an occlusion 5 at the level of the nasopharynx 1, where an elongated and/or floppy soft palate 6 has collapsed against a thickened posterior pharyngeal wall 22. FIG. 4 shows an occlusion 5 at the level of the oropharynx and nasopharynx 1 and 2, where both an elongated soft palate 6, base of tongue 16 and a floppy epiglottis 12 have collapsed against the pharyngeal wall 22.

With reference to FIGS. 1-4, the nasopharynx 1 is the portion of the pharynx at the level or above the soft palate 6. In the nasopharynx, a deviated nasal septum or enlarged nasal turbinates 10 may occasionally contribute to upper airway resistance or blockage. Rarely, a nasal mass, such as a polyp, cyst or tumor may be a source of obstruction. The oropharynx 2 includes structures from the soft palate 6 to the upper border of the epiglottis 12 and includes the inferior surface of the hard palate 14, tongue 16, tonsils 18, palatoglossal arch 20, the posterior pharyngeal wall 22 and the mandible 24. The mandible typically has a bone thickness of about 5 mm to about 10 mm anteriorly with similar thicknesses laterally. An obstruction in the oropharynx 2 may result when the tongue 16 is displaced posteriorly during sleep as a consequence of reduced muscle activity during deep or non-REM sleep. The displaced tongue 16 may push the soft palate 6 posteriorly and may seal off the nasopharynx 1 from the oropharynx 2. The tongue 16 may also contact the posterior pharyngeal wall 22, which causes further airway obstruction.

The hypopharynx 3 includes the region from the upper border of the epiglottis 12 to the inferior border of the cricoid cartilage 14. The hypopharynx 3 further includes the hyoid bone 28, a U-shaped, free-floating bone that does not articulate with any other bone. The hyoid bone 28 is attached to surrounding structures by various muscles and connective tissues. The hyoid bone 28 lies inferior to the tongue 16 and superior to the thyroid cartilage 30. A thyrohyoid membrane 17 and a thyrohyoid muscle 18 attaches to the inferior border of the hyoid 28 and the superior border of the thyroid cartilage 30. The epiglottis 12 is infero-posterior to the hyoid bone 28 and attaches to the hyoid bone by a median hyoepiglottic ligament. The hyoid bone attaches anteriorly to the infero-posterior aspect of the mandible 24 by the geniohyoid muscle.

The invention provides a method of maintaining airway patency in an airway of a patient by implanting one or more devices into airway-forming tissue and permitting a bioerodable portion of the device to bioerode, thereby applying a force to the airway-forming tissue to maintain airway patency due to, e.g., a curvature, length or width change in the device. In some embodiments, the device or devices are implanted without initially affixing the device to the tissue. Over time, tissue ingrowth into the devices may provide some fixation of the devices to the airway-forming tissue prior to the bioerosion and the device shape change. Various embodiments of shape-changing implants may be used to practice the invention, and the devices may be implanted into various parts of the patient's airway-forming tissue, as needed.

Figure 5A:
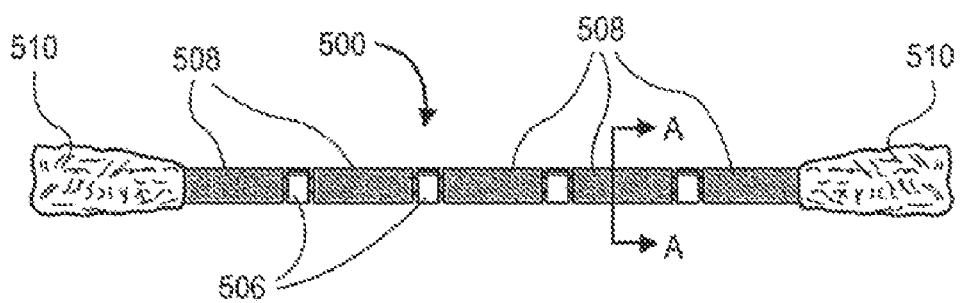
FIGS. 5A-C show an airway-maintaining device according to one embodiment of the invention.
Figure 5B:
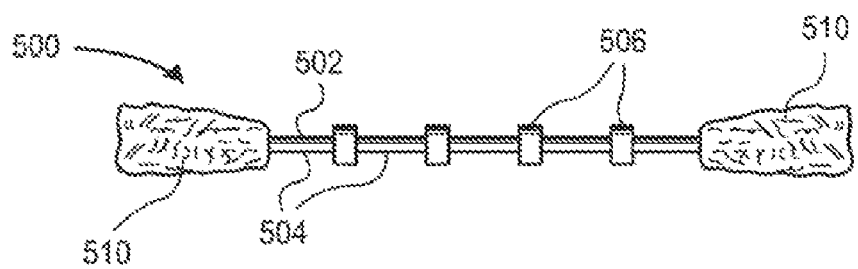
Figure 5C:
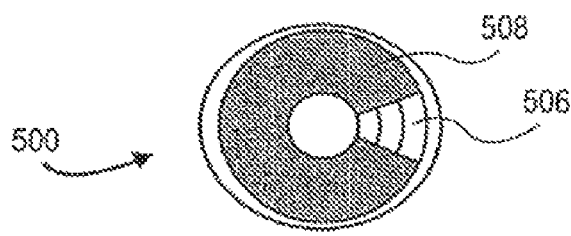

FIGS. 5A-C show one embodiment of a device 500 that may be implanted in airway-forming tissue to maintain patency of the patient's airway. Device 500 has a body 502 with a plurality of narrow sections 504 separated by wide sections 506. As shown, the narrow and wide sections are cylindrical, although other shapes may be used. The body 502 may be made of a resiliently deformable material, such as silicone rubber, polyurethanes or other resiliently deformable polymer or a coil of stainless steel, spring steel, or superelastic nickel-titanium alloy or other resiliently deformable metal, or a composite of the resiliently deformable polymer and metal.

FIG. 5B shows body 502 in its at-rest shape. In FIG. 5A, body 502 has been stretched to a deformed shape. Spacers 508 formed from a bioerodable or bioabsorbable material (such as, e.g., polycaprolactone, polylactic acid, polyglycolic acid, polylactide coglycolide, polyglactin, poly-L-lactide, polyhydroxalkanoates, starch, cellulose, chitosan, or structural protein) have been inserted between wide sections 506 to maintain the device in its deformed shape. In this embodiment, the spacers 508 are injection molded and have a C shape, although other manufacturing techniques and other shapes may be used as desired.

Anchors 510 are formed at both ends of body 502. In this embodiment, anchors 510 are formed from a non-woven fabric (such as polypropylene, polyethylene, or polyester) to promote tissue ingrowth. Other anchors may be used, as desired.

Device 500 may be implanted in a patient's airway-forming tissue in the deformed shape shown in FIG. 5A. In some embodiments, the device 500 is not affixed to the airway-forming tissue when implanted. Over time, tissue may grow into the fabric of anchors 510 to at least partially affix the device to the airway-forming tissue. Also over time, the bioerodable spacers 508 will bioerode, thereby permitting device 500 to move back toward the at-rest form shown in FIG. 5A. As it attempts to return to its at-rest shape, device 500 exerts a force on the airway-forming tissue into which it is implanted to maintain the patient's airway in a patent condition.

FIGS. 6A-J show various other embodiments of the invention in their deformed states. As in the embodiment of FIG. 5, these devices for maintaining patency of an airway may be implanted into airway-forming tissue of the patient in the illustrated deformed state. Over time, tissue may grow into the device anchors and possibly other parts of the device to at least partially affix the device to the airway-forming tissue. Also over time, the bioerodable spacer portions of the device may bioerode, thereby permitting the device to attempt to move toward a shorter at-rest shape, thereby exerting a force on the airway-forming tissue into which it is implanted to maintain the patient's airway in a patent condition. The deformable bodies of these devices may be formed, e.g., of silicone rubber.

In FIGS. 6A-B, device 600 has a stiff bioerodable fiber 608 helically wound within narrow sections 604 of a resiliently deformable body 602 between wide sections 606 to maintain body 602 in its stretched deformed state. Fiber 608 may be made, e.g., of polyglactin 910, which is a copolymer of 90% glycolide and 10% L-lactide. When fiber 608 bioerodes, body 602 will attempt to shorten to its at-rest shape. Anchors 610 are disposed at both ends of body 602. Anchors 610 may be formed from woven polyester, polyethylene or polypropylene to provide for tissue ingrowth.

FIGS. 6C-D show a device 611 having a resiliently deformable body 612 in which a plurality elongated openings 614 are formed. In the depicted deformed state, bioerodable, rod shaped, spacers 618 (formed from, e.g., polylactidecoglycolide (PLG)) are disposed in the openings 614 to maintain the body's elongated deformed shape. Paddle-shaped anchor regions 620 having a plurality of holes or depressions 619 are disposed at both ends of body 612. Holes or depressions 619 permit tissue in-growth. Anchor regions 620 may be integral with the central portion of body 612 or may be formed from a different material, such as reinforced polyester. Anchor regions also may be integral with the central portion of body 612 and contain a composite reinforcing element such as a polyester fabric.

FIGS. 6E-F show a device 621 similar to that shown in FIGS. 5A-C in which the bioerodable portion 628 is formed of a helically wound bioerodable fiber, such as that discussed above with respect to FIGS. 6A-B and contains anchoring regions 630 of nonwoven fabric (e.g. polyester, polyethylene, or polypropylene).

FIGS. 6G-H show a device 631 having a resiliently deformable body 632 similar to body 602 of FIG. 6A. As shown, body 632 is in a stretched deformed shape. Bioerodable spacers 638 (similar to those of the embodiment shown in FIG. 5A) are disposed in narrow portions 634 between wide portions 636 to maintain body in this stretched shape. Anchors 640 on both ends are formed from an open or closed cell foam material to promote tissue in-growth.

FIGS. 6I-J show a device 641 substantially the same as the device shown in FIGS. 6E-F with the exception of the anchors 649 and 650. In this embodiment, anchors 649 and 650 are self-expanding baskets that can be compressed to the form shown as anchor 650 during implantation and will self-expand toward the at-rest shape shown as anchor 649 after deployment. The open areas of the anchors provide material loops and spaces for tissue ingrowth and attachment.

Other embodiments of the airway maintaining device may use various aspects of the illustrated embodiments as needed. For example, the anchors at end of the device body may differ from each other.

Figure 7A:
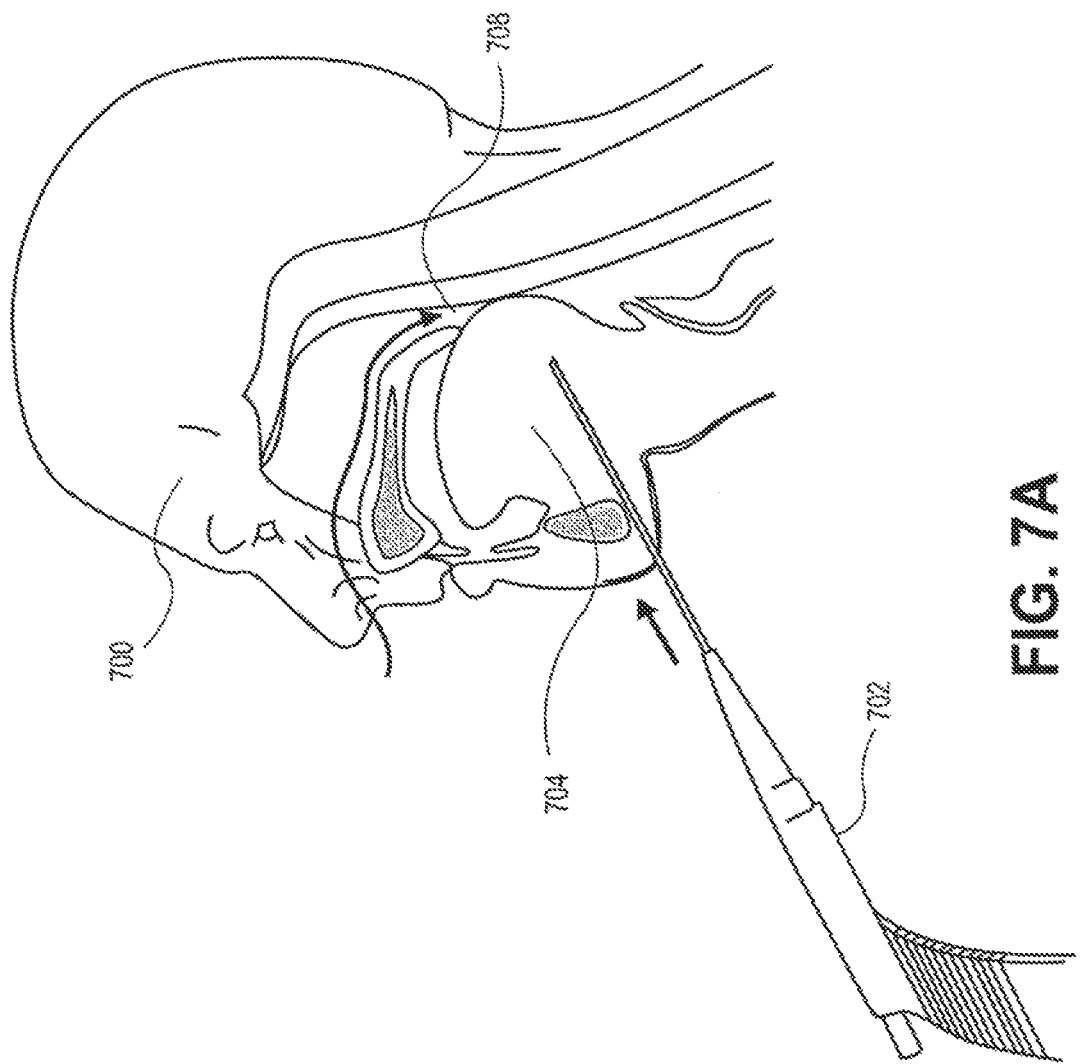
FIGS. 7A-C show implantation and use of an airway-maintaining device delivered submandibularly.
Figure 7B:
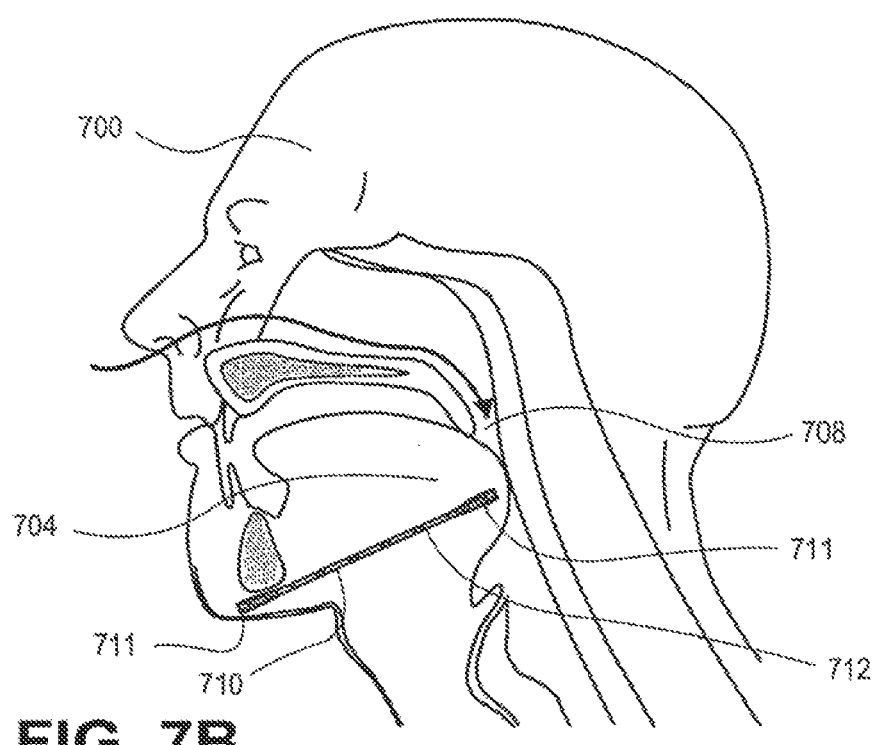
Figure 7C:
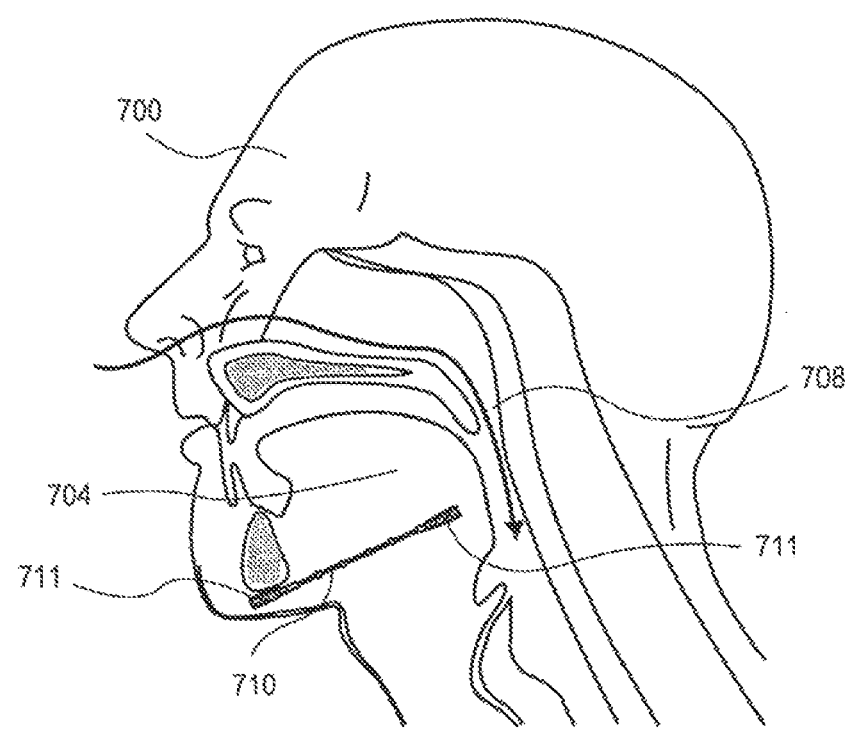

FIGS. 7-9 illustrate therapy provided by embodiments of this invention. In FIGS. 7A-C, a delivery tool 702 has been inserted submandibularly into the patient 700 to deliver an airway maintaining device 710 into a region of the patient's tongue 704 forming part of the patient's airway 708, which is shown as being blocked in FIG. 7A. Device 710 may be, e.g., any of the devices discussed above with respect to FIGS. 5 and 6. As shown in FIG. 7B, the device 710 is delivered in an elongated deformed state. In some embodiments, device 710 when first delivered is not affixed to the tongue tissue. Over time, however, tissue may grow into the anchors 711 of device 710 and/or other parts of the device. Also over time, bioerodable portions 712 of device 710 will bioerode, thereby permitting device 710 to move toward a shorter at-rest shape, thereby applying a force to the patient's tissue to maintain the patency of the airway, as shown in FIG. 7C.

Figure 8A:
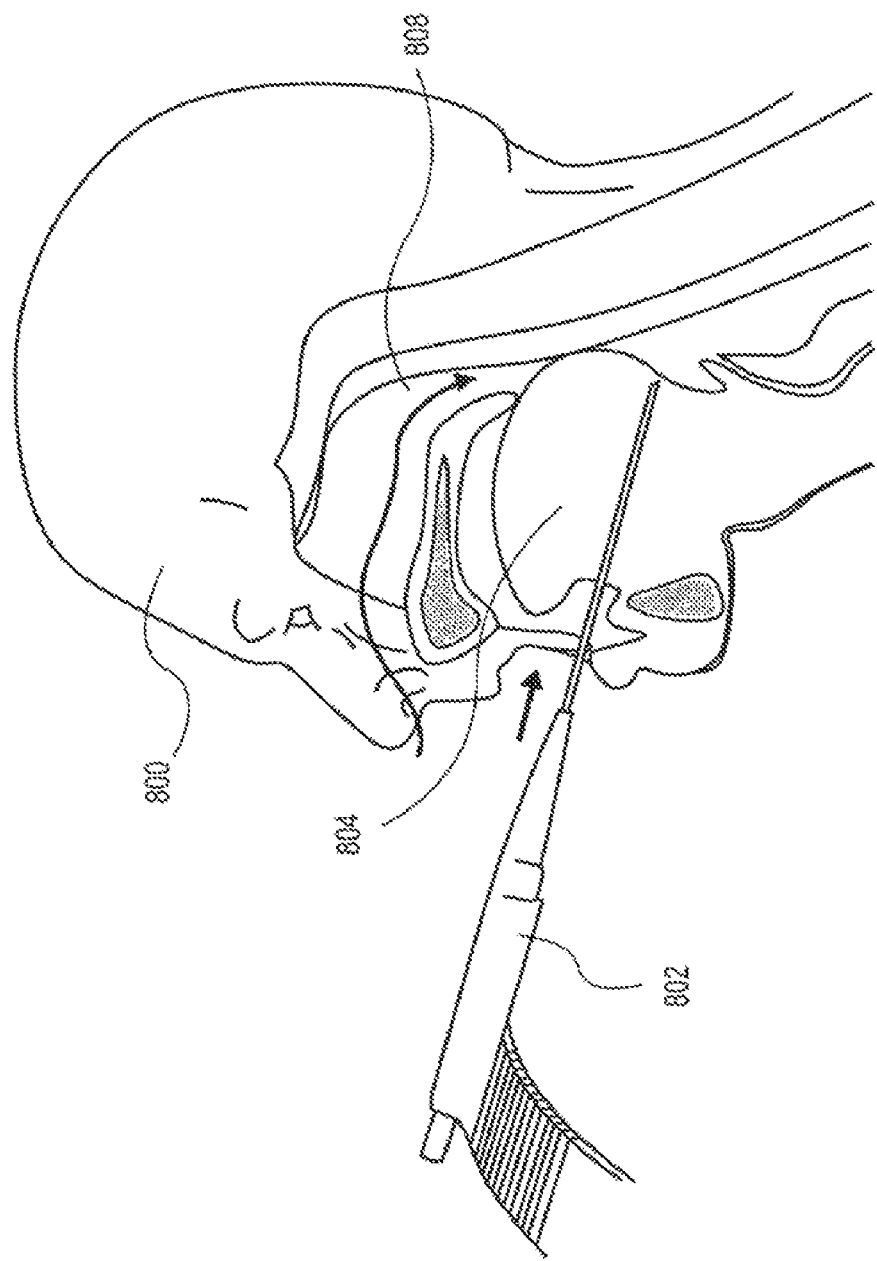
FIGS. 8A-C show implantation and use of an airway-maintaining device delivered intraorally and sublingually.
Figure 8B:
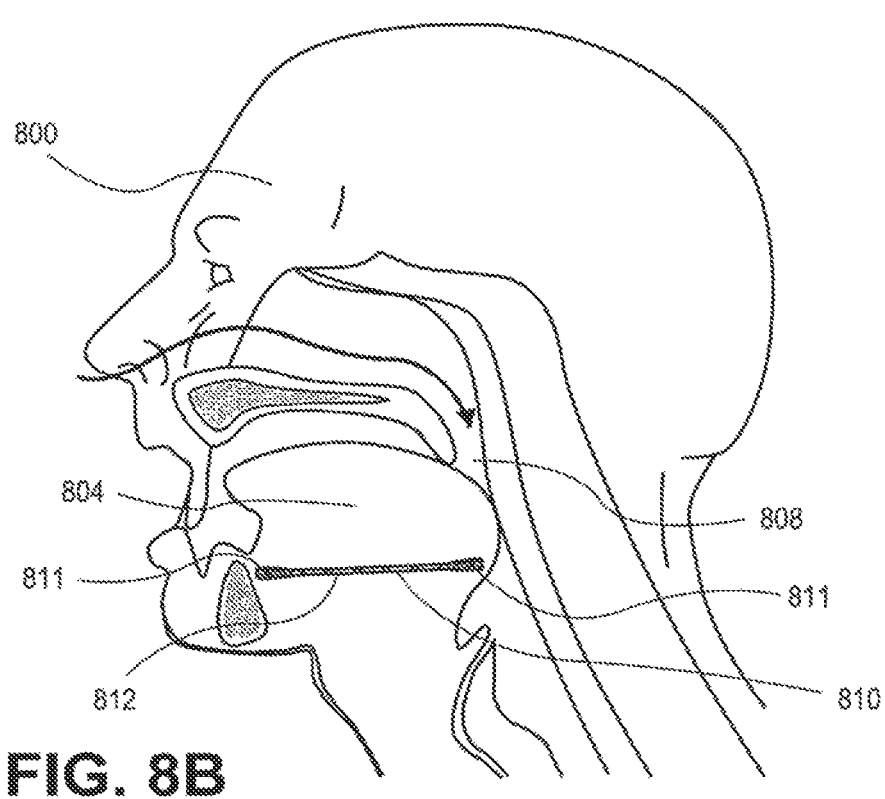
Figure 8C:
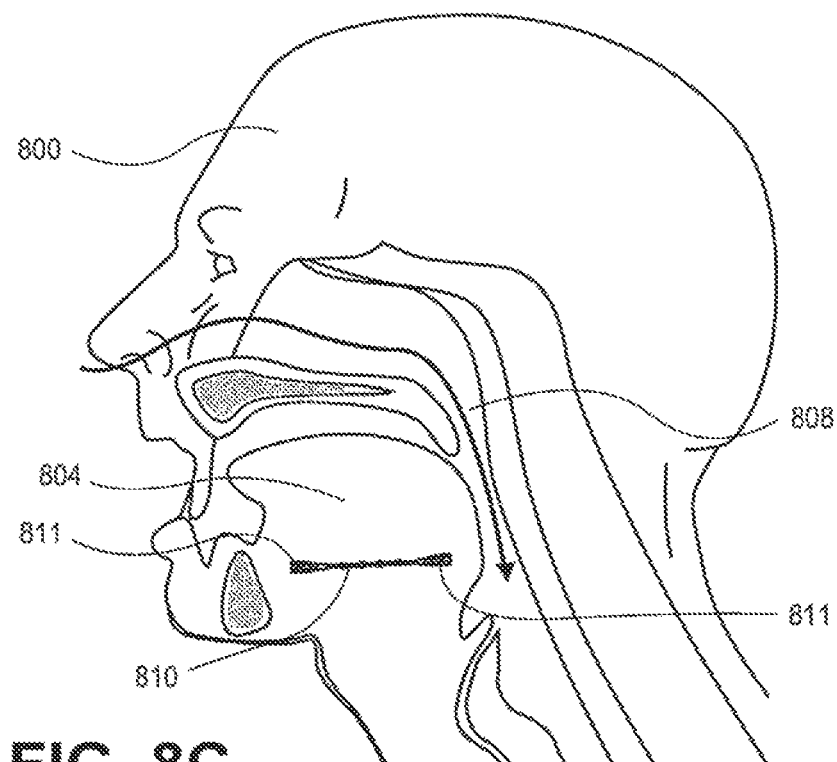

In FIGS. 8A-C, a delivery tool 802 has been inserted intraorally and sublingually into the patient 800 to deliver an airway maintaining device 810 into a region of the patient's tongue 804 forming part of the patient's airway 808, which is shown as being blocked in FIG. 8A. Device 810 may be, e.g., any of the devices discussed above with respect to FIGS. 5 and 6. As shown in FIG. 8B, the device 810 is delivered in an elongated deformed state. In some embodiments, device 810 when first delivered is not affixed to the tongue tissue. Over time, however, tissue may grow into the anchors 811 of device 810 and/or other parts of the device. Also over time, bioerodable portions 812 of device 810 will bioerode, thereby permitting device 810 to move toward a shorter at-rest shape, thereby applying a force to the patient's tissue to maintain the patency of the airway, as shown in FIG. 8C.

Figure 9B:
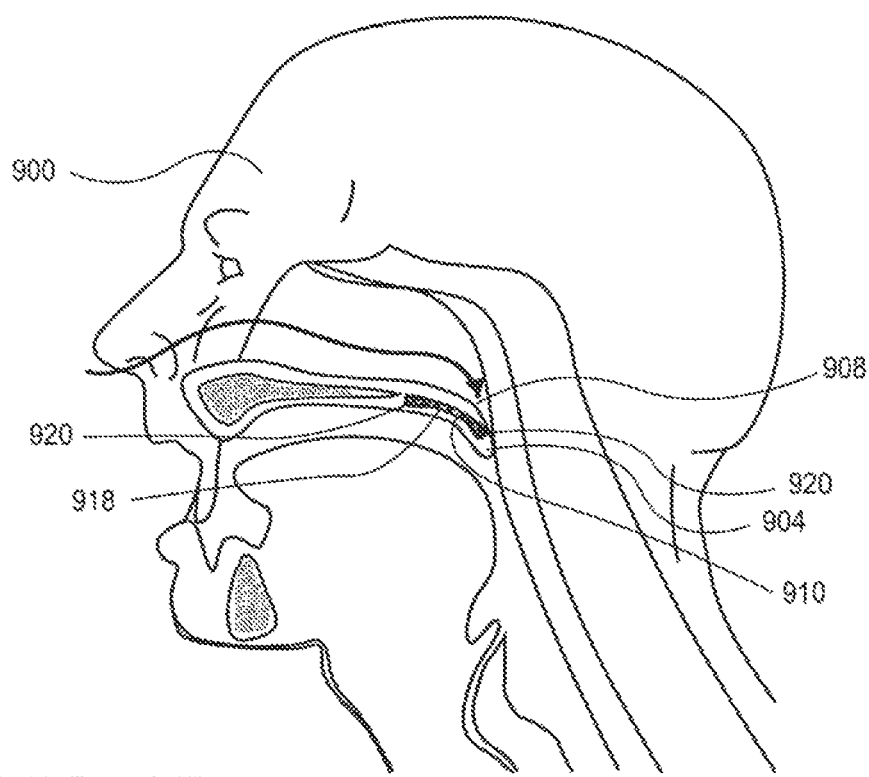
Figure 9C:
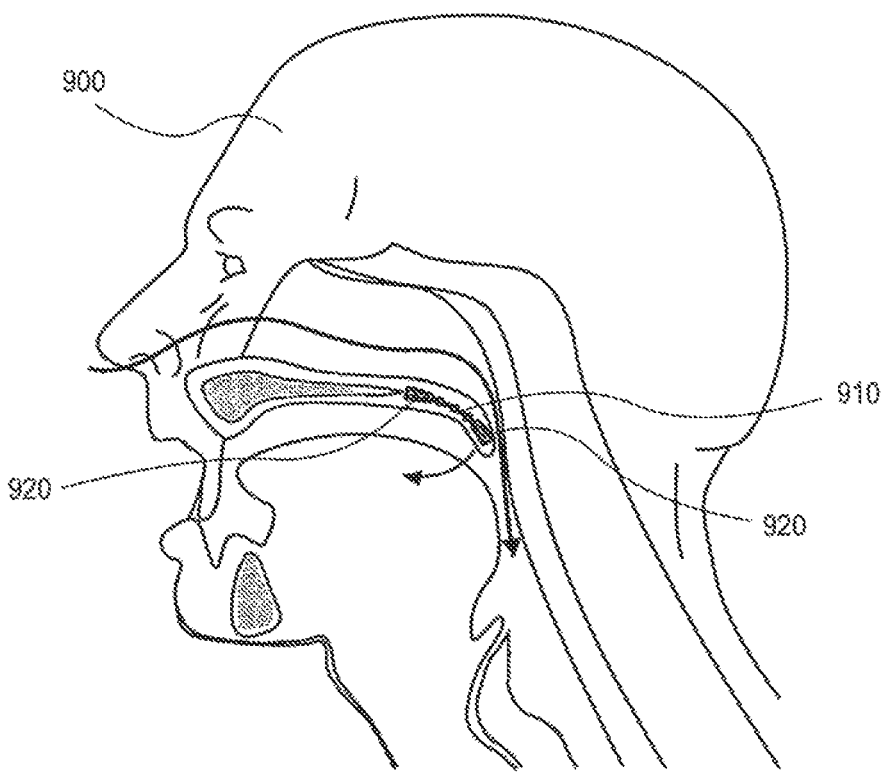

In FIGS. 9A-C, a delivery tool 902 has been inserted intraorally into the patient 900 to deliver an airway maintaining device 910 into a region of the patient's soft palate 904 forming part of the patient's airway 908, which is shown as being blocked in FIG. 9A. Device 910 is described in further detail below with respect to FIGS. 10 and 11. As shown in FIGS. 9B and 11A, the device 910 is delivered in an elongated and straightened deformed state. In some embodiments, device 910 when first delivered is not affixed to the soft palate tissue. Over time, however, tissue may grow into the anchors 920 of device 910 and/or other parts of the device. Also over time, bioerodable portions 918 of device 910 will bioerode, thereby permitting device 910 to move toward a shorter and more curved at-rest shape, thereby applying a force to the patient's soft palate tissue to maintain the patency of the airway, as shown in FIGS. 9C and 11B.

Figure 10A:
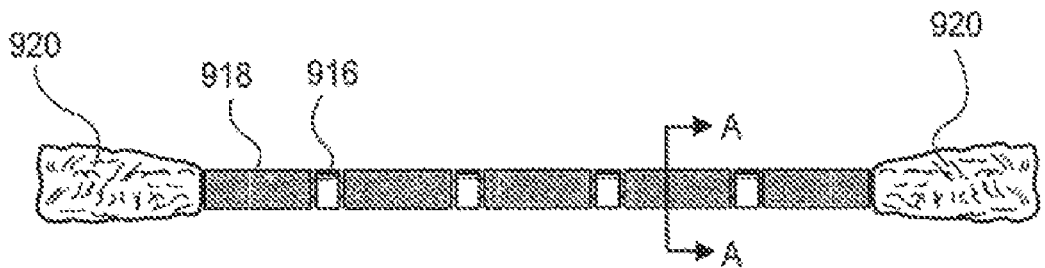
FIGS. 10A-C show details of the device shown in FIG. 9.
Figure 10B:
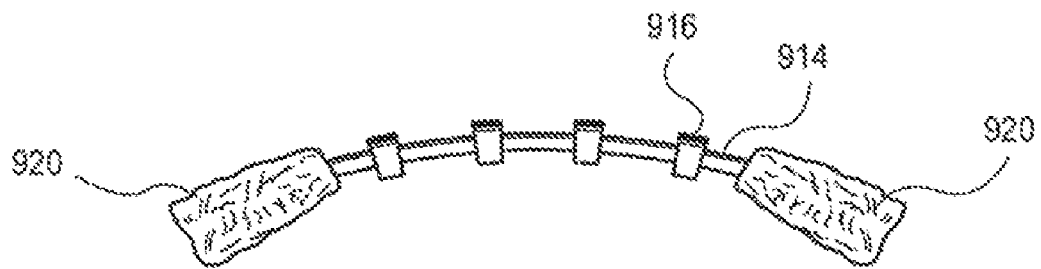
Figure 10C:
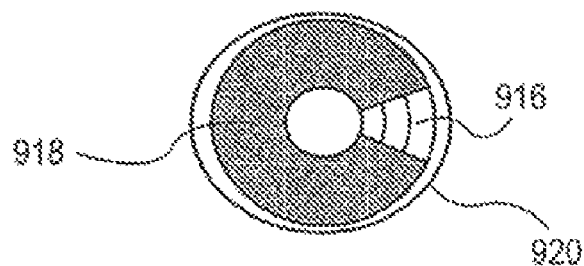
Figure 11A:
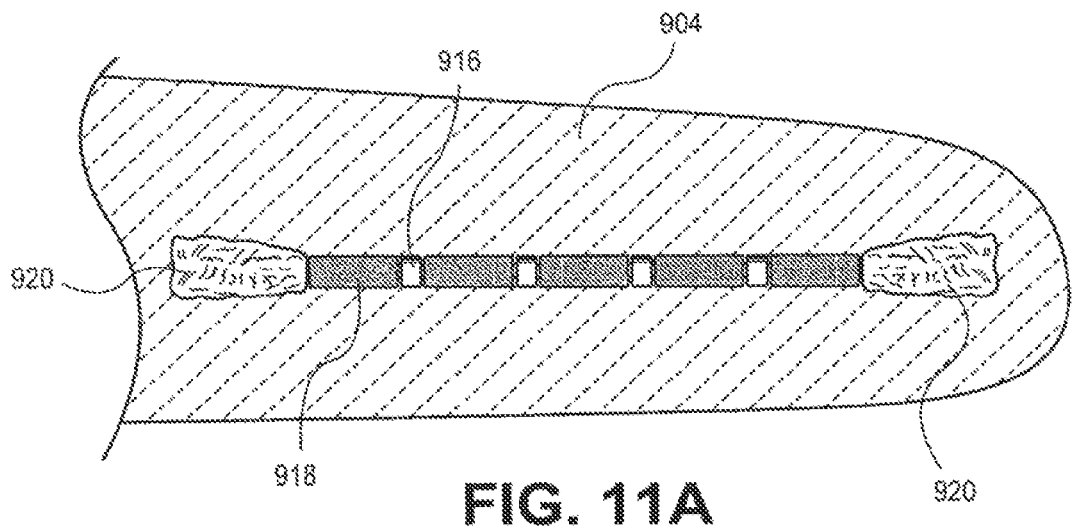
FIGS. 11A-B show details of the device shown in FIGS. 9 and 10 in place in the soft palate.
Figure 11B:
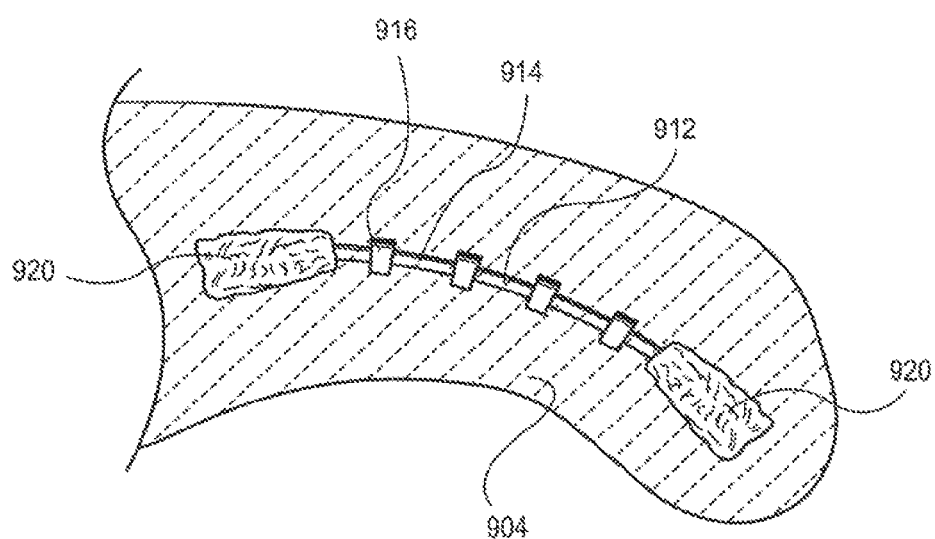

FIGS. 10A-C and 11A-B show more details of an airway-maintaining device 910 suitable for implantation in the soft palate. The device's deformed shape is shown in FIGS. 10A and 11A. In this shape, spacers 918 formed from a bioerodable material are disposed in narrow regions 914 of body 912 between wide regions 914 of body 912. Body 912 is formed from a resiliently deformable material (such as, e.g., silicone rubber, polyurethanes or other resiliently deformable polymer or a coil of stainless steel, spring steel, or superelastic nickel-titanium alloy or other resiliently deformable metal, or a composite of the resiliently deformable polymer and metal.) and is deformed into the straight and elongated form shown in FIGS. 10A and 11A. The shorter and more curved at-rest shape of body 912 is shown in FIG. 10B. This is the shape the device will attempt to return to after the bioerodable portions 916 bioerode, thereby exerting force on the airway-forming tissue of the soft palate, as shown in FIG. 11B. In this embodiment, anchors 920 are formed from a non-woven fabric (such as polypropylene or polyester) to promote tissue ingrowth. Other anchors may be used, as desired. In this embodiment, the spacers 918 are injection molded from polycaprolactone, polylactic acid, polyglycolic acid, polylactide coglycolide, polyglactin, poly-L-lactide and have a C shape, although other manufacturing techniques (e.g., dipping processes for applying the spacers over the resiliently deformable polymer or metal), materials, and other shapes may be used as desired.

Figure 12A:
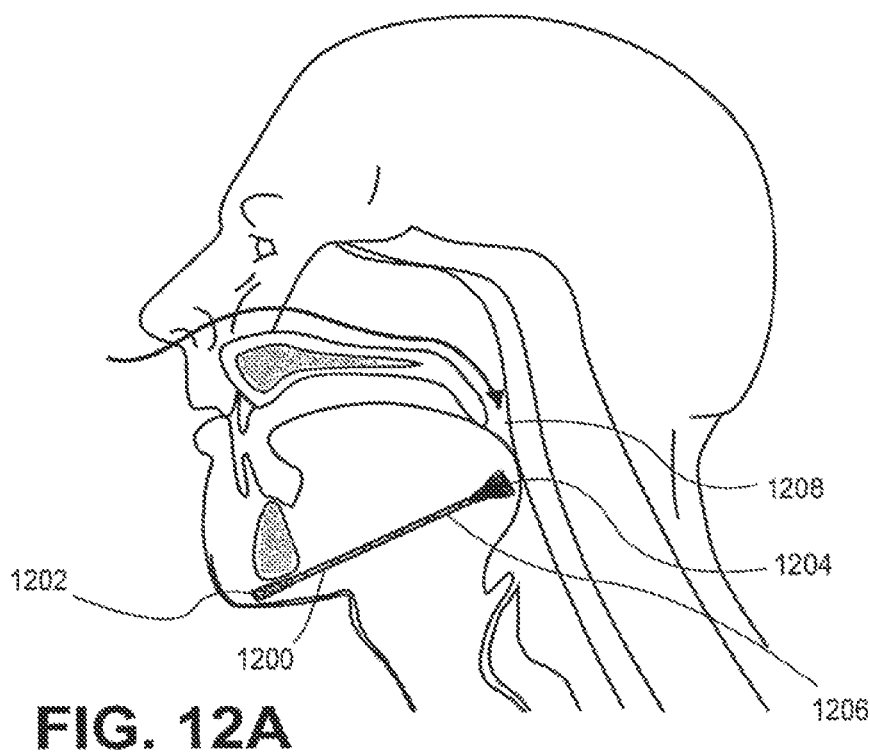
FIGS. 12A-B show an airway maintaining device according to yet another embodiment of the invention in place in the patient.
Figure 12B:
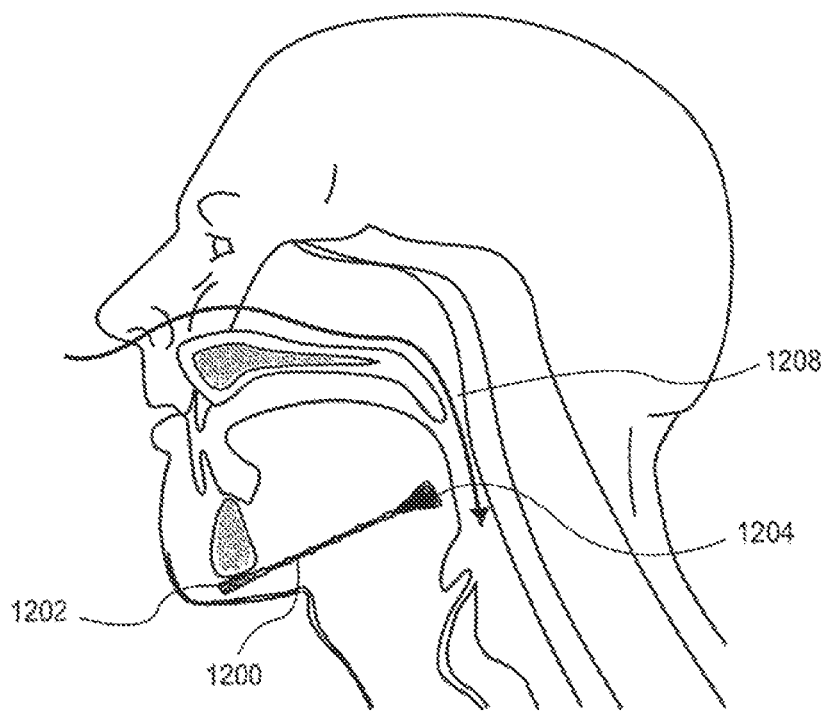

FIGS. 12A-B show another embodiment of an airway maintaining device 1200 implanted submandibularly into tongue tissue 1201 forming part of the patient's airway. Device 1200 has anchors 1202 and 1204 which differ from each other. Anchor 1204 is an expandable anchor, such as the self-expandable anchor 649 described above with respect to FIG. 6I, whereas anchor 1202 is not expandable. As shown in FIG. 12A, device 1200 when implanted into tissue 1201 is in an elongated deformed shape. Over time, bioerodable portions 1206 of device 1200 will bioerode, and device 1200 will attempt to return to its shorter at-rest shape, thereby exerting a force on tissue 1201 to maintain the patency of airway 1208, as shown in FIG. 12B.

Figure 13:
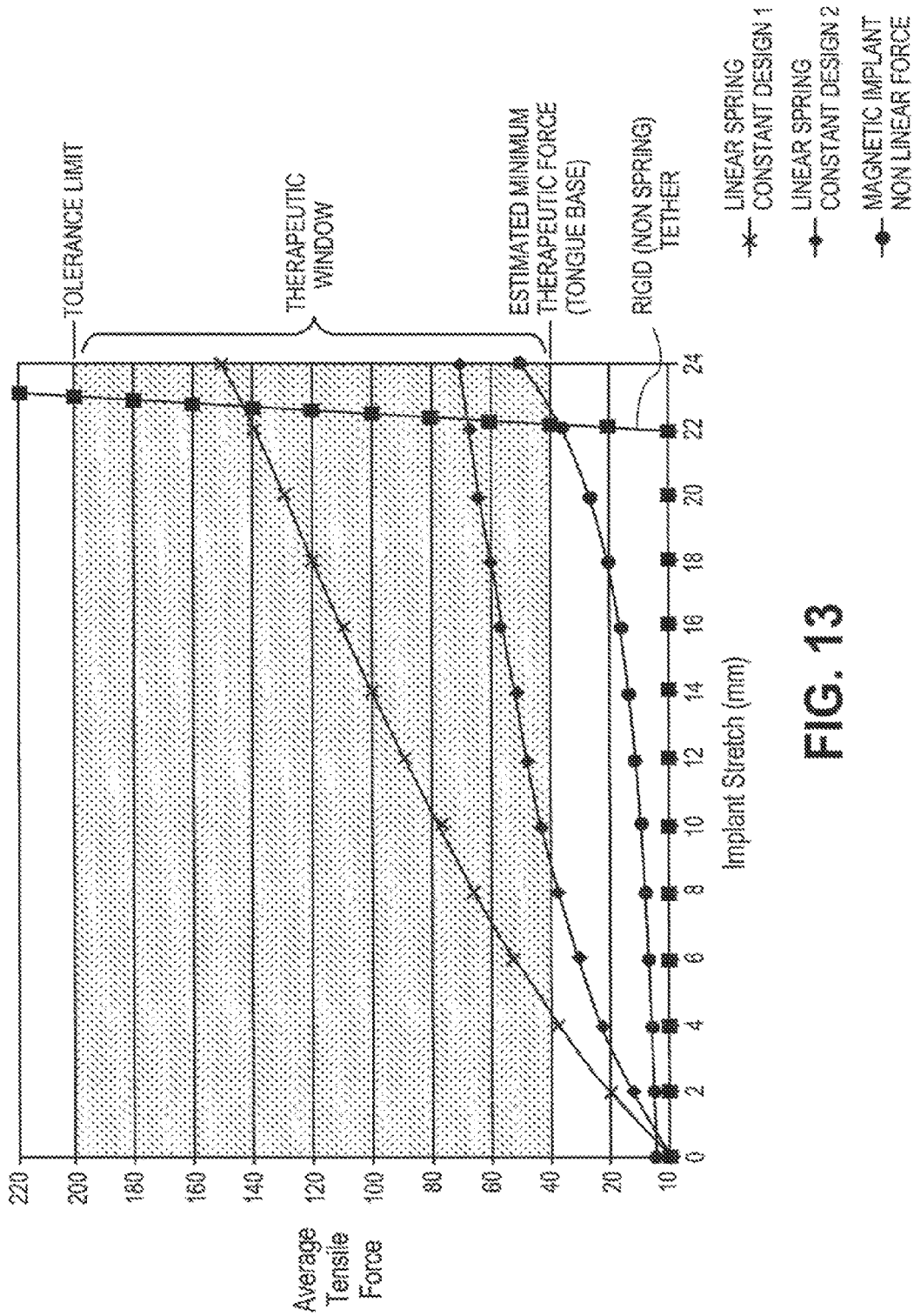
FIG. 13 is a graph comparing tensile force applied by embodiments of the invention and theoretical force applied by other obstructive sleep apnea therapy devices.
Figure 14A:
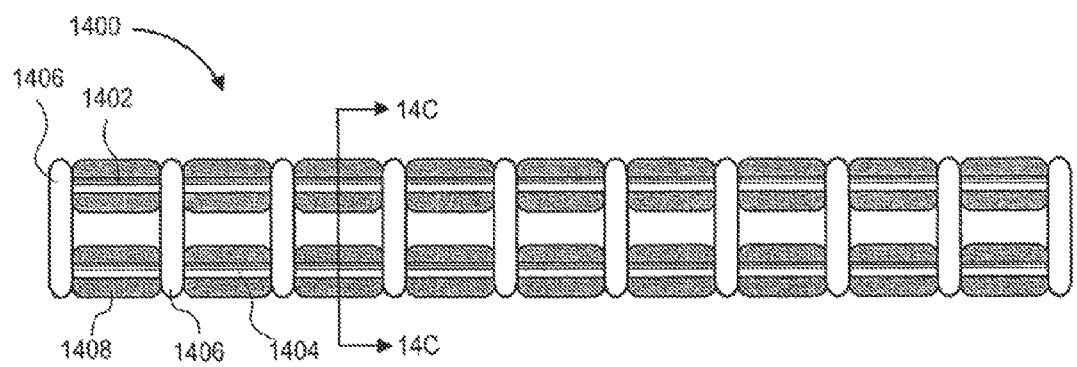
FIGS. 14A-C show an airway-maintaining device according to still another embodiment of the invention.
Figure 14B:
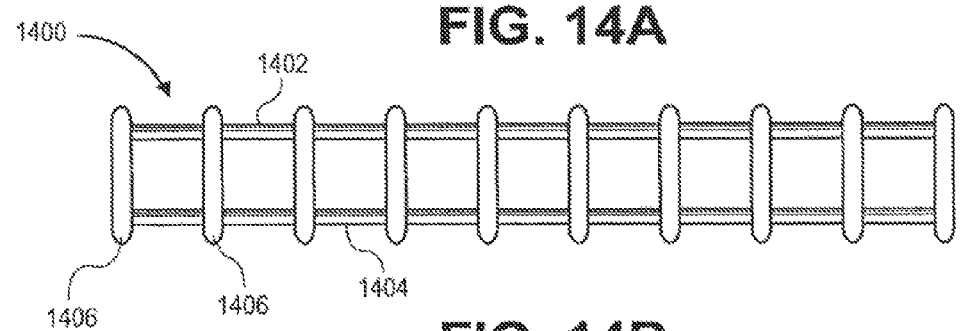
Figure 14C:
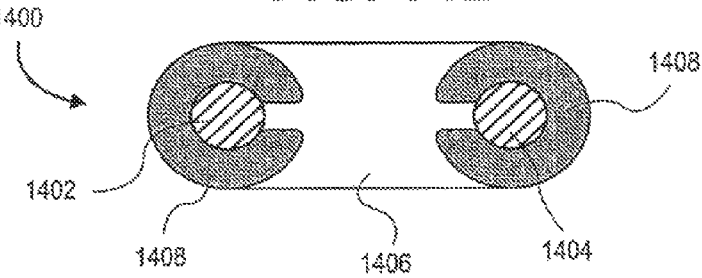

FIG. 13 is a graph comparing theoretical average tensile force provided to patient airway-forming tissue by various implantable obstructive sleep apnea therapy devices respect to the amount of stretching experienced by the implant. Tether devices are shown by the two lines formed by the square data points. As can be seen, such rigid devices provide no tensile force on the patient's tissue until all slack has been removed, at which point the tether provides a nearly infinite force, possibly exceeding the patient's tolerance limit.

The curve formed by the round data points show theoretical tensile force applied by magnet-based obstructive sleep apnea implants. As can be seen, such devices have a very narrow operational range falling with the therapeutic range providing a benefit to the patient through the application of a minimum therapeutic force.

The curves formed by the diamond and cross data points show theoretical tensile forces applied by two airway-maintaining devices according to this invention having two different spring constants in their deformable device bodies. As shown, these devices can be designed so that they provide beneficial airway maintenance therapy to the patient over a wide range of lengths.

Figure 15A:
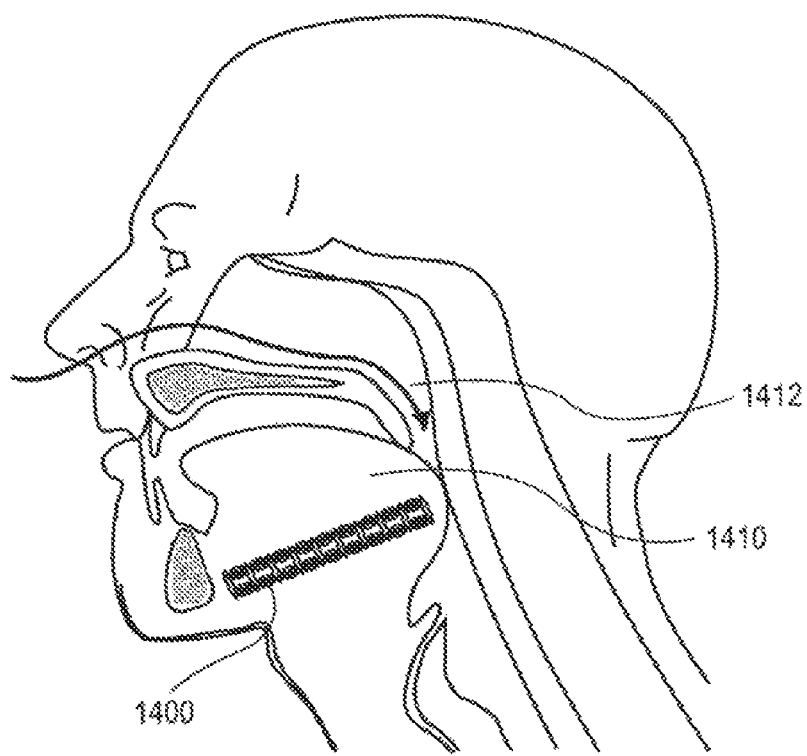
FIGS. 15A-B show the device of FIG. 14 in place in patient.
Figure 15B:
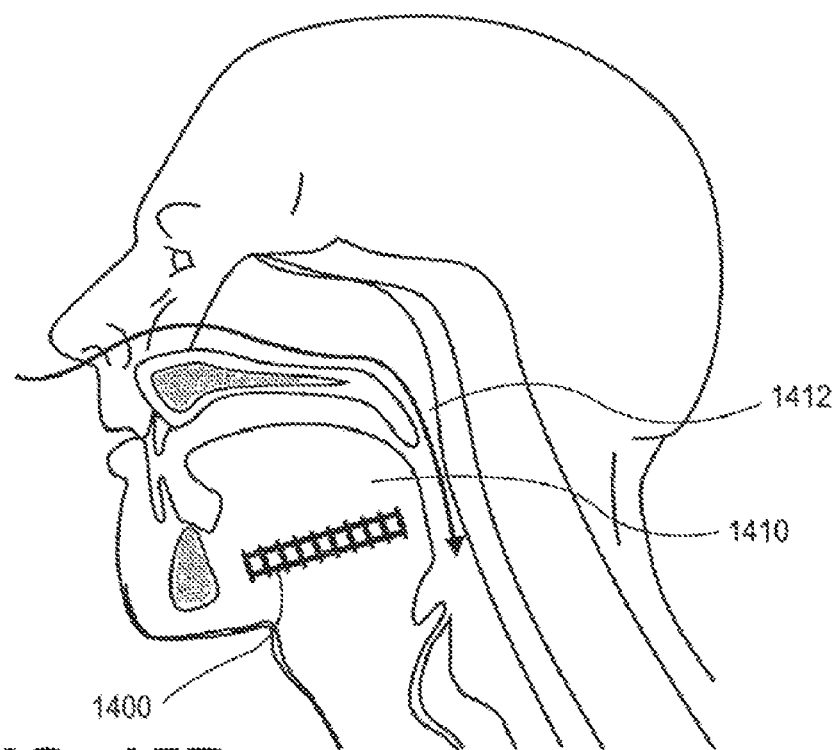

FIGS. 14A-C and 15A-B show yet another embodiment of the invention. Device 1400 has a device body with two elongate rails 1402 and 1404 formed from a resiliently deformable material, such as silicone rubber. A plurality of spaced-apart oval flanges 1406 are attached to rails 1402 and 1404. In the deformed state shown in FIGS. 14A and 15A, C-shaped bioerodable spacers 1408 are disposed between adjacent flanges 1406 to maintain the device in its elongated shape. When spacers 1408 bioerode over time, device 1400 moves toward the at-rest shape shown in FIG. 14B, thereby exerting a force on the patient's airway forming tissue (shown as the tongue 1410 in FIG. 15) to maintain patency of the airway 1412 as shown in FIG. 15B.

Figure 16A:
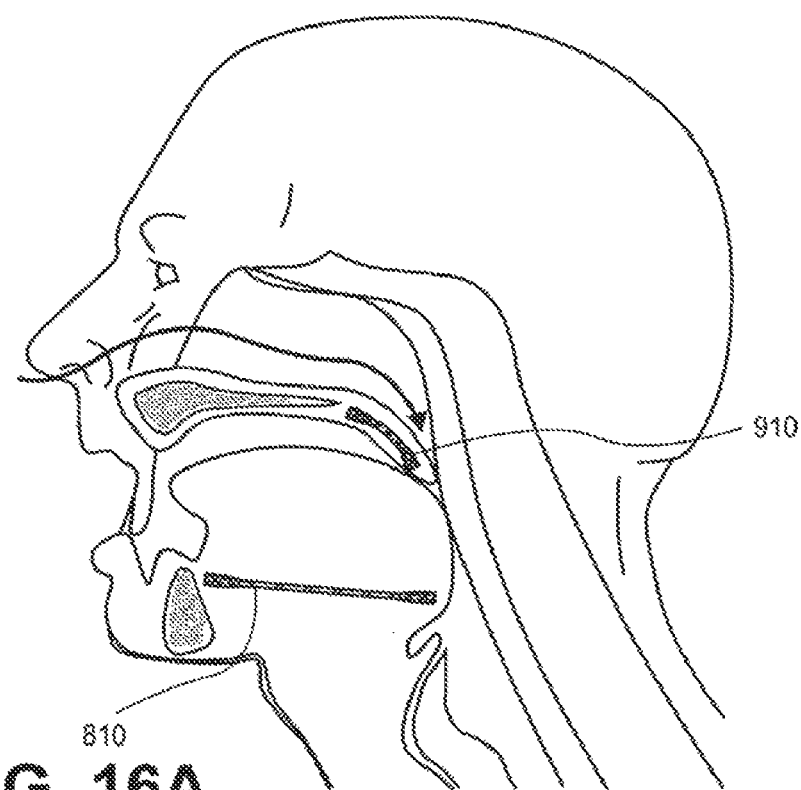
FIGS. 16A-B show the devices of FIGS. 8 and 9 in place in a patient.
Figure 16B:
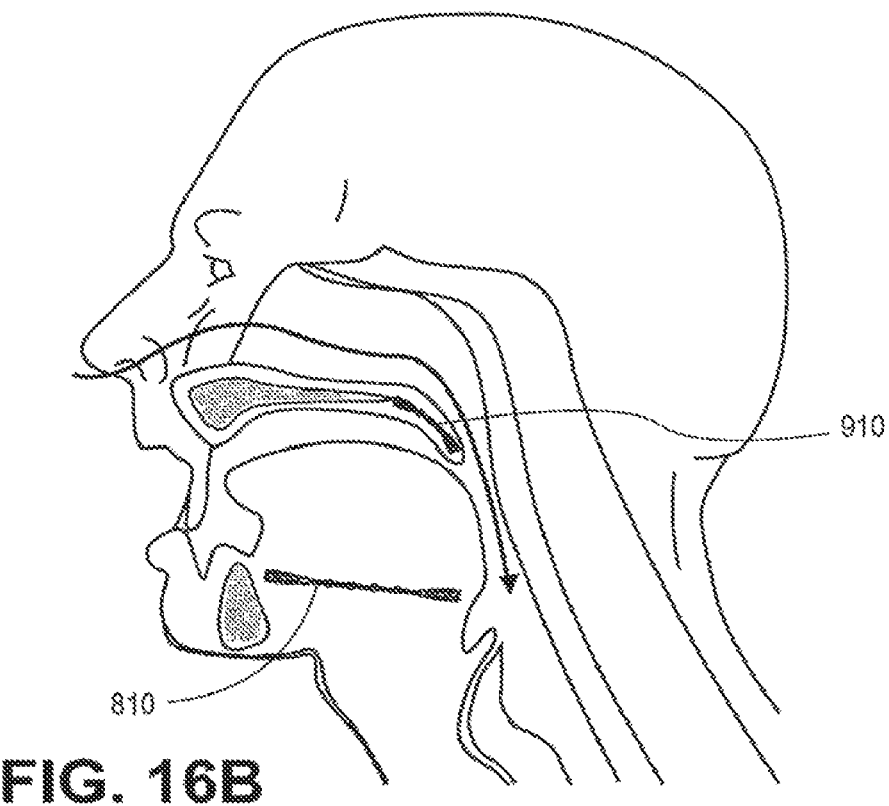

FIGS. 16A-B demonstrate how multiple airway-maintaining devices may be implanted into a single patient, such as the tongue device 810 and the soft palate device 910 described with respect to FIGS. 8 and 9 above, respectively.

Figure 17A:
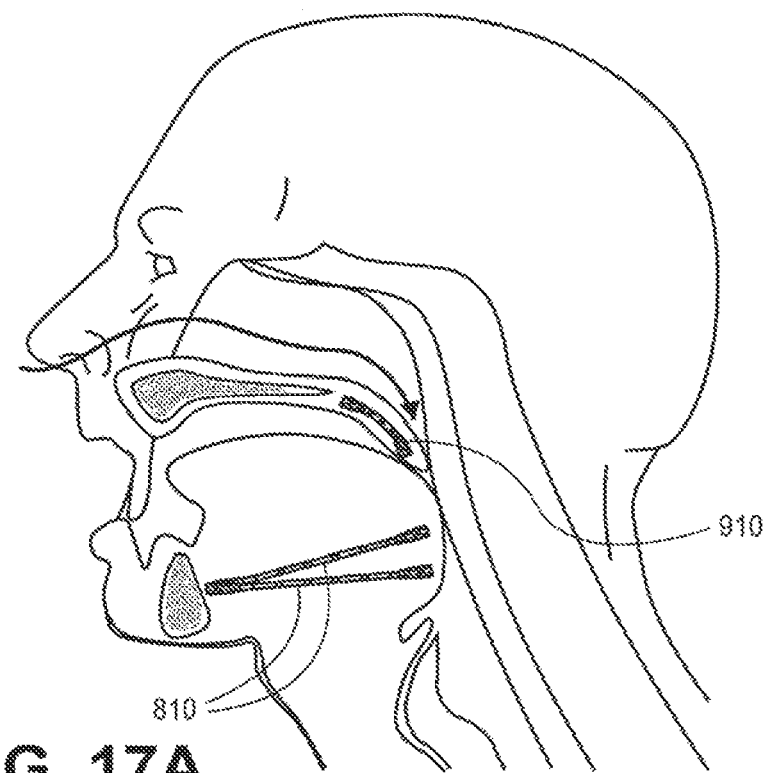
FIGS. 17A-E show multiple devices, such as those of FIGS. 8 and 9, in place in a patient.
Figure 17B:
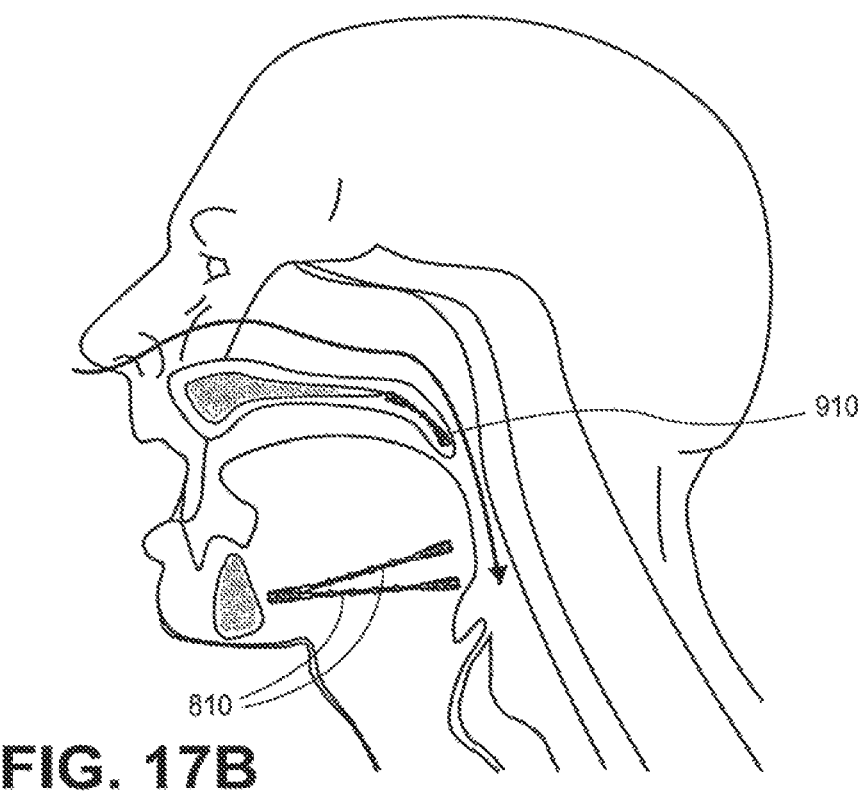
Figure 17C:
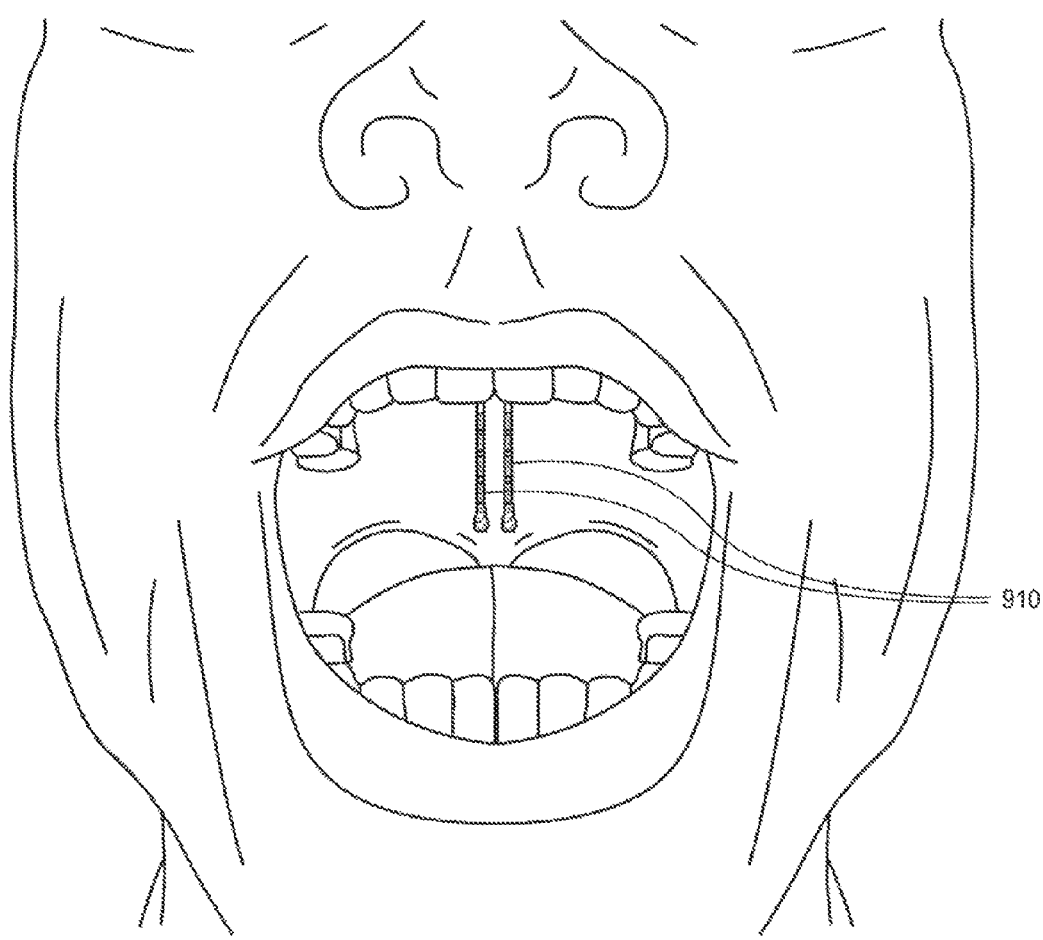
Figure 17D:
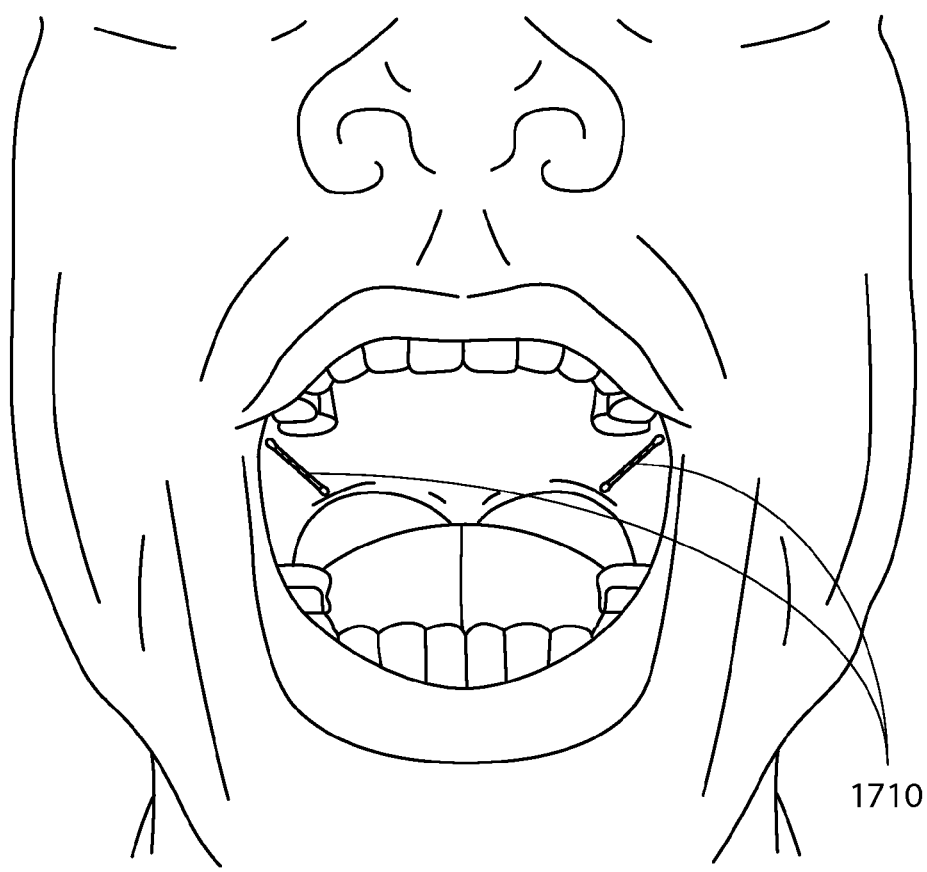
Figure 17E:
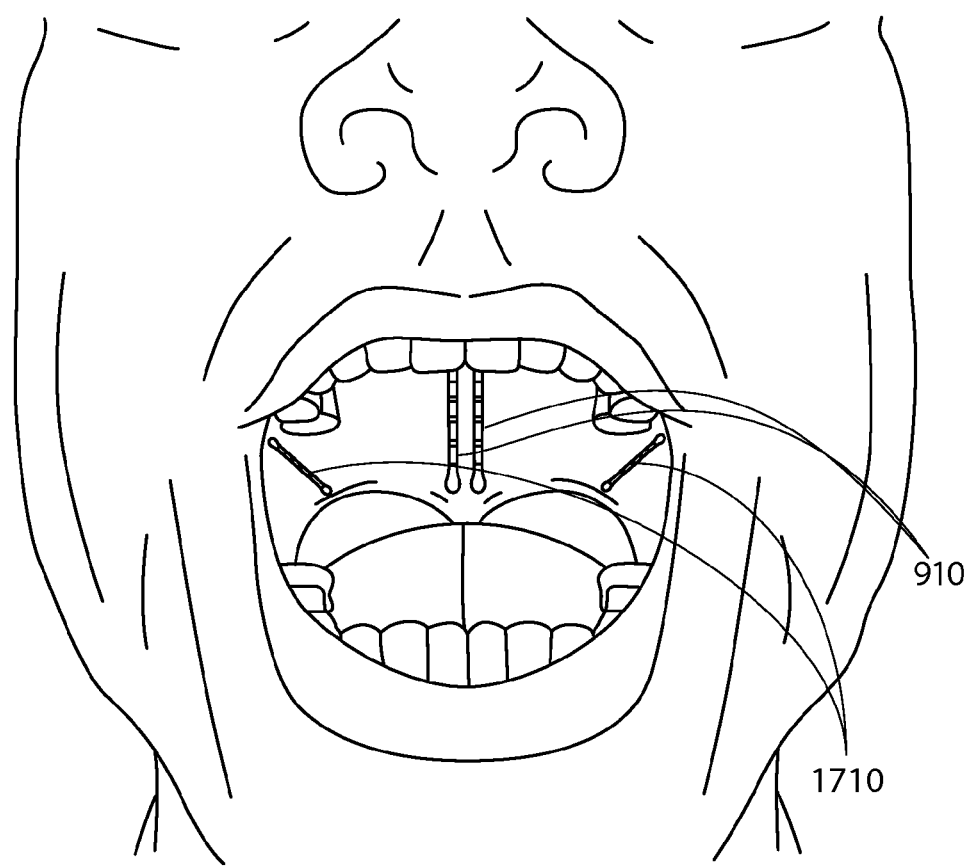

Likewise, FIGS. 17A-E show how multiple airway-maintaining devices may be implanted into the same region of airway-forming tissue, such as tongue devices 810 shown in FIGS. 17A-B, soft palate devices 910 shown in FIGS. 17A-C, and similar pharyngeal wall devices 1710 shown in FIGS. 17D-E.

Figure 18A:
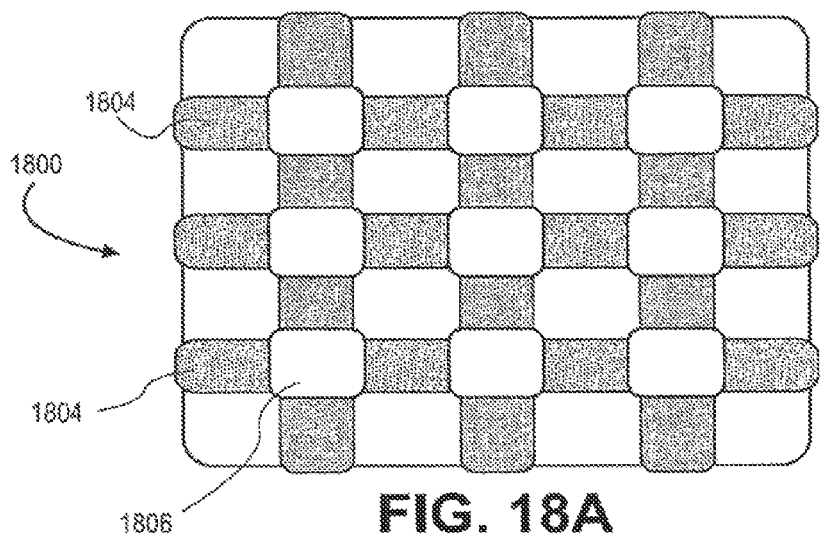
FIGS. 18A-C show another embodiment of the airway maintaining device of this invention.
Figure 18B:
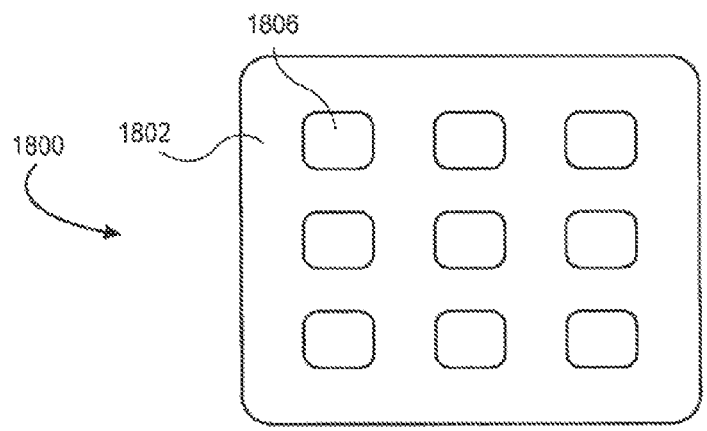
Figure 18C:
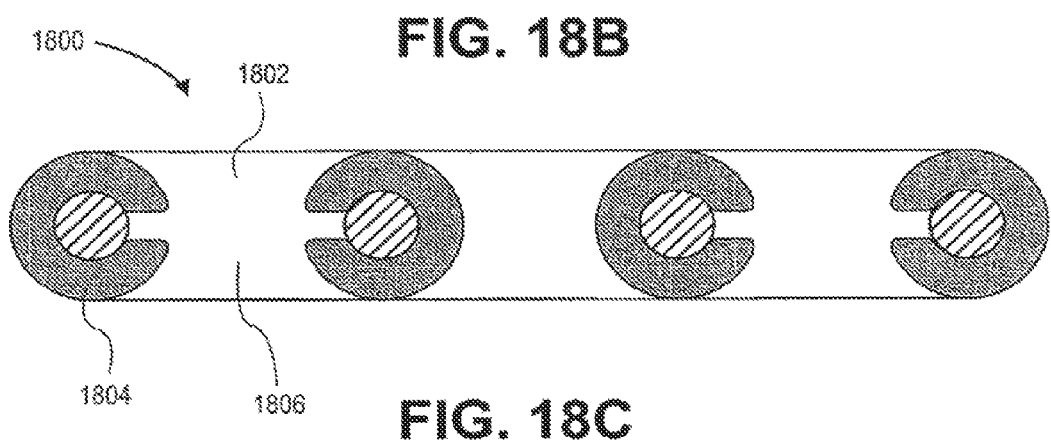

FIG. 18A-C show an embodiment of an airway-maintaining device 1800 in which the deformed state of the device body 1802 shown in FIG. 18A is both longer and wider than the at-rest state of the device body 1802 shown in FIG. 18B. Bioerodable spacers 1802 are disposed in openings 1804 formed in resiliently deformable body 1802. As the spacers erode, the body 1802 will move toward its at-rest shape. The openings in the deformed and at rest shapes 1804 and 1806 constitute anchoring elements. This embodiment could be placed in an anatomical structure such as the soft palate and could exert force on the airway forming tissue in two directions to maintain patency.

In some embodiments, the device may include one or more bioactive agents in the bioerodable portion(s). Bioactive agents such as drugs or hormones that are eluted during the course of erosion of the bioerodable materials, may serve, for example, to promote healing of the implant wound, or to promote stabilization of the implanted device within the tissue site by, for example, promoting the toughening the fibrotic tissue capsule that forms around the implanted device.

What is claimed is:

1. A method of maintaining airway patency in an airway of a patient, the method comprising:
   implanting a device into tissue adjacent an airway, the device having a bioerodable material helically wound around a resiliently deformable body to temporarily maintain the deformable body in a stretched, deformed state; and
   permitting the bioerodable material of the device to bioerode to release the deformable body from its stretched, deformed state, thereby allowing the deformable body to apply a force to maintain airway patency.

2. The method of claim 1 further comprising releasing a bioactive agent from the bioerodable material as it bioerodes.

3. The method of claim 1 wherein the force is applied to airway-forming tissue.

4. The method of claim 1 further comprising expanding a portion of the device during the implanting step.

5. The method of claim 1 wherein the implanting step comprises inserting the device into the patient submandibularly.

6. The method of claim 1 wherein the implanting step comprises inserting the device into the patient sublingually.

7. The method of claim 1 wherein the implanting step comprises inserting the device into the patient intra-orally.

8. The method of claim 1 wherein the permitting step comprises changing a shape of the device when the bioerodable material bioerodes.

9. The method of claim 8 wherein the changing step comprises changing a length of the device.

10. The method of claim 1 further comprising permitting newly formed tissue to grow into open areas of anchors of the device prior to applying a force to airway-forming tissue.

11. The method of claim 1 wherein the implanting step comprises inserting the device into tongue tissue.

12. The method of claim 1 wherein the implanting step comprises inserting the device into soft palate tissue.

13. The method of claim 1 wherein the implanting step comprises inserting the device into pharyngeal wall tissue.

14. A method of maintaining airway patency in an airway of a patient, the method comprising:
   implanting a device into tissue adjacent an airway, the device having a bioerodable material wound around a resiliently deformable body to temporarily maintain the deformable body in a stretched, deformed state; and
   permitting the bioerodable material of the device to bioerode to release the deformable body from its stretched, deformed state, thereby allowing the deformable body to apply a force to maintain airway patency,
   wherein the implanting step further comprises a device having a bioerodable material helically wound within a narrow section of a resiliently deformable body between wide sections of the body.

15. The method of claim 14 wherein the implanting step further comprises a device having a plurality of bioerodable material portions, a plurality of narrow sections and a plurality of wide sections, each of the plurality of bioerodable material portions being helically wound within one of the narrow sections of the resiliently deformable body between two of the wide sections of the body.

16. A device for maintaining patency of an airway of a patient comprising:
   a resiliently deformable body having an at-rest shape and a deformed shape, the body being adapted to be implanted into tissue adjacent an airway of the patient;
   proximal and distal anchors adapted to be implanted into the tissue and adapted to affix to the tissue; and
   at least one bioerodable material portion helically wound around a portion of the body, the bioerodable material portion maintaining the body in the deformed shape against a return force; the body being configured to return toward the at-rest shape upon erosion of the bioerodable material portion,
   wherein the bioerodable material portion is a fiber.

17. The device of claim 16 further comprising an elutable bioactive agent associated with the bioerodable material portion.

18. The device of claim 16 wherein the deformed shape is longer than the at-rest shape.

19. The device of claim 16 wherein the body is sized and shaped to be inserted into tongue tissue.

20. The device of claim 16 wherein the body is sized and shaped to be inserted into soft palate tissue.

21. The device of claim 16 wherein the body is sized and shaped to be inserted into pharyngeal tissue.

22. The device of claim 16 wherein the proximal and distal anchors are adapted to be implanted into the tissue without affixing the device to the tissue upon implantation, and wherein the anchors are adapted to allow newly formed tissue to grow into open areas of the anchors to affix the anchors to the tissue adjacent the airway.

23. The device of claim 16 wherein at least one of the proximal and distal anchors is adapted to expand.

24. The device of claim 16 wherein at least one of the proximal and distal anchors is adapted to self-expand.

25. The device of claim 16 wherein at least one of the anchors contains at least one through hole.

26. A device for maintaining patency of an airway of a patient comprising:
   a resiliently deformable body having an at-rest shape and a deformed shape, the body being adapted to be implanted into tissue adjacent an airway of the patient;
   proximal and distal anchors adapted to be implanted into the tissue and adapted to affix to the tissue;
   at least one bioerodable material portion wound around a portion of the body, the bioerodable material portion maintaining the body in the deformed shape against a return force; the body being configured to return toward the at-rest shape upon erosion of the bioerodable material portion,
   wherein the at least one bioerodable material portion is helically wound within a narrow section of the body between wide sections of the body.

27. The device of claim 26 wherein the device comprises a plurality of bioerodable material portions, a plurality of narrow sections and a plurality of wide sections, each of the plurality of bioerodable material portions being helically wound within one of the narrow sections of the body between two of the wide sections of the body.

28. A device for maintaining patency of an airway of a patient comprising:

a resiliently deformable body having an at-rest shape and a deformed shape, the body being adapted to be implanted into tissue adjacent an airway of the patient;
proximal and distal anchors adapted to be implanted into the tissue and adapted to affix to the tissue;
at least one bioerodable material portion helically wound around a portion of the body, the bioerodable material portion maintaining the body in the deformed shape against a return force; the body being configured to return toward the at-rest shape upon erosion of the bioerodable material portion,
wherein the at least one bioerodable material portion is formed from a polymer.

* * * * *